United States Patent
Hiatt et al.

[11] Patent Number: 6,136,568
[45] Date of Patent: Oct. 24, 2000

[54] DE NOVO POLYNUCLEOTIDE SYNTHESIS USING ROLLING TEMPLATES

[76] Inventors: Andrew C. Hiatt, 660 Torrance St., San Diego, Calif. 92103; Floyd D. Rose, 117 Via de la Valle, Del Mar, Calif. 92014

[21] Appl. No.: 08/929,856

[22] Filed: Sep. 15, 1997

[51] Int. Cl.[7] .............................. C12Q 1/68; C12P 19/34; C07H 19/00; C07H 21/04
[52] U.S. Cl. .......................... 435/91.1; 435/6; 435/91.2; 435/810; 536/22.1; 536/24.3; 536/23.1; 536/24.31; 536/25.3
[58] Field of Search ............................... 435/6, 91.1, 91.2, 435/810; 536/22.1, 24.3, 23.1, 24.31, 24.33, 25.3

[56] References Cited

U.S. PATENT DOCUMENTS

| | | | |
|---|---|---|---|
| 4,734,363 | 3/1988 | Dattagupta et al. | 435/91 |
| 4,994,368 | 2/1991 | Goodman et al. | 435/6 |
| 5,169,766 | 12/1992 | Schuster et al. | 435/91 |
| 5,302,509 | 4/1994 | Cheeseman | 435/6 |
| 5,397,698 | 3/1995 | Goodman et al. | 435/6 |
| 5,407,799 | 4/1995 | Studier | 435/6 |
| 5,436,143 | 7/1995 | Hyman | 435/91.2 |
| 5,516,664 | 5/1996 | Hyman | 435/91.52 |
| 5,518,900 | 5/1996 | Nikiforov et al. | 435/91.1 |
| 5,599,921 | 2/1997 | Sorge et al. | 536/24.33 |
| 5,602,000 | 2/1997 | Hyman | 435/91.1 |

*Primary Examiner*—Jezia Riley
*Attorney, Agent, or Firm*—Lerner, David, Littenberg, Krumholz & Mentlik, LLP

[57] ABSTRACT

Disclosed is a method for synthesizing polynucleotide molecules such as genes or gene segments. A primer having 5' and 3' ends is incubated with a relatively shorter template having a 5' region non-complementary to the primer, a 3' region complementary to the 3' end of the primer, and a non-reactive 3' terminus to allow the 3' region of the template to anneal to the primer. The annealed product is reacted with at least one nucleotide in the presence of a template-dependent polynucleotide polymerase to produce a primer extended at its 3' end by at least one nucleotide complementary to the 5' region of the template. The extended primer is then dissociated from the template. The extended primer is further extended by repeating this cycle for sufficient cycles, wherein the templates and enzymes may differ from cycle to cycle, to obtain the object polynucleotide. Also disclosed are template libraries and kits containing said libraries for use in conjunction with the polynucleotide synthesis method.

41 Claims, 1 Drawing Sheet

DE NOVO POLYNUCLEOTIDE SYNTHESIS USING ROLLING TEMPLATES

FIELD OF THE INVENTION

This invention relates to the synthesis of polynucleotides using template dependent enzymes.

BACKGROUND OF THE INVENTION

Oligonucleotides have been synthesized in vitro using organic synthesis methods. These methods include the phosphoramidite method described in Adams et al., J. Amer. Chem. Soc., 105:661 (1983), and Froehler et al., Tetrahedron Lett., 24:3171 (1983) and the phosphotriester method described in German Offenlegungsscript 264432. Organic synthesis methods using H-phosphonates are also described in Froehler et al., as well as in U.S. Pat. No. 5,264,566.

The phosphoramidite method of phosphodiester bond formation and oligonucleotide synthesis represents the current procedure of choice employed by most laboratories for the coupling of desired nucleotides without the use of a template. In this method, the coupling reaction is initiated by a nucleoside attached to a solid support. The 5'-hydroxyl group of the immobilized nucleoside is free for coupling with the second nucleoside of the chain to be assembled. Because the growing oligonucleotide chain has a 5'-hydroxyl available for reaction with a mononucleoside, the direction of synthesis is referred to as 3' to 5'.

Each successive mononucleoside to be added to the growing oligonucleotide chain contains a 3'-phosphoramidate moiety which reacts with the 5'-hydroxyl group of the support-bound nucleotide to form a 5' to 3' internucleotide phosphodiester bond. The 5'-hydroxyl group of the incoming mononucleoside is protected, usually by a trityl group, in order to prevent the uncontrolled polymerization of the nucleosides. After each incoming nucleoside is added, the protected 5'-hydroxyl group is deprotected, so that it is available for reaction with the next incoming nucleoside having a 3'-phosphoramidite group and a protected 5'-hydroxyl. This is followed by deprotection and addition of the next incoming nucleotide. Between each nucleoside addition step, unreacted chains which fail to participate in phosphodiester bond formation with the desired nucleoside are chemically "capped" to prevent their further elongation. This usually involves chemical acetylation.

A drawback to the phosphoramidite method, as well as to virtually all chemical methods of phosphodiester bond formation, is that the reaction must be performed in organic solvents and in the absence of water. Many of these organic solvents are toxic or otherwise hazardous. Another drawback to chemical synthesis is that each addition or cycle is at best 98 percent efficient. That is, following each nucleotide addition, at least 2 percent of the growing oligonucleotide chains are capped, resulting in a yield loss. The total yield loss for the nucleotide chain being synthesized thus increases with each nucleotide added to the sequence. For example, assuming a yield of 98 percent per nucleotide addition, the synthesis of a polynucleotide consisting of 70 mononucleotides would result in a yield loss of approximately 75 percent. Thus, the object nucleotide chain would have to be isolated from a reaction mixture of polynucleotides, 75 percent of which would consist of capped oligonucleotides ranging between 1 and 69 nucleotides in length.

Thus, a need exists for a method of synthesizing polynucleotides which improves the efficiency of phosphodiester bond formation and is capable of producing shorter chain oligonucleotides in higher yields and longer chain polynucleotides in acceptable yields. There is also a need for a polynucleotide synthesis system which is compatible with pre-existing polynucleotides, such as vector DNAs, so that a desired polynucleotide can be readily added onto the pre-existing molecules. The phophoramidite method is not compatible with "add-on" synthesis to pre-existing polynucleotides.

Enzyme catalyzed phosphodiester bond formation can be performed in an aqueous environment utilizing either single or double stranded oligo- or polynucleotides as reaction initiators. These reaction conditions also greatly reduce the use of toxic and/or hazardous materials. The 3' to 5' direction of synthesis inherent to the phosphoramidite method of phosphodiester bond formation, however, cannot be enzyme catalyzed. All known enzymes capable of catalyzing the formation of phosphodiester bonds do so in the 5' to 3' direction because the growing polynucleotide strand always projects a 3'-hydroxyl available for attachment of the next nucleoside. There are many classes of enzymes capable of catalyzing the formation of phosphodiester bonds. The polymerases are largely template dependent because they add a complementary nucleotide to the 3' hydroxyl of the growing strand of a double stranded polynucleotide. The template independent polymerases primarily catalyze the formation of single stranded nucleotide polymers. The ligases are template independent enzymes and form a phosphodiester bond between two polynucleotides or between a polynucleotide and a mononucleotide.

Use of a template independent polymerase requires protection of the 3'-hydroxyl of the mononucleotide in order to prevent multiple phosphodiester bond formations and hence repeated mononucleotide additions. This approach requires the synthesis of nucleotides which are not normally utilized by the polymerase. These modified nucleotides tend to adversely affect the reaction rate. The template independent approach is also hampered by the commercial availability of only a single template independent polymerase, namely terminal deoxynucleotidyl transferase (EC 2.7.7.31). Thus, there is a further need for a system which can utilize template dependent polymerases but does not require the use of modified nucleotides.

There are many available template dependent polymerases having various characteristics useful for de novo synthesis of polynucleotide chains. Template-dependent polymerases (TDPs) have traditionally been used for a variety of synthetic protocols that involve copying preexisting DNA or RNA strands. These protocols fall into five categories, -namely primer extension or PCR (e.g., *PCR Technology: Principles and Applications for DNA Amplification*, H. S. Erlich (ed.), IRL Press at Oxford University Press, Oxford, England (1989)); mutagenesis (e.g., Smith. M., "In vitro mutagenesis", Annu. Rev. Genet. 19:423–462 (1985)); Sanger-type sequencing techniques (e.g., H. G. Griffin, A. M. Griffin, *DNA Sequencing Protocols: Methods in Molecular Biology*, Vol. 23, The Humana Press, Totowa, N.J. (1993)); "filling-in" techniques (e.g., J. Sambrook, E. F. Fritsch, and T. Maniatis, *Molecular Cloning: A Laboratory Manual*, Cold Spring Harbor Laboratory, Cold Spring Harbor, N.Y. (1989)); and replacement synthesis (e.g., Sambrook et al., supra.). None of these categories, however, contemplate the use of a template-dependent polymerase for the creation of an original polynucleotide strand for which a complete complementary template strand is non-existent. Thus, an even further need exists for a method of synthesizing an object polynucleotide sequence which is not a strict complementary copy of any single pre-existing template, using a template dependent polymerase.

In sum, current gene synthesis technology is expensive, error-prone and very time consuming. The inaccuracy of these techniques is exacerbated because sequence errors are not usually detected until after the gene is cloned and expressed. At that time, correcting errors involves discarding all the work and starting over. Thus, having fast access to synthetic genes, whose sequences are assured, and at a reasonable price, would move de novo gene construction from a last resort to the method of choice for analysis of the function of gene products.

SUMMARY OF THE INVENTION

Applicant has invented a fast, accurate and inexpensive method of synthesizing polynucleotides such as RNA and DNA, featured by rolling templates that successively direct the addition of one or more nucleotides to a relatively longer, polynucleotide primer strand. Accordingly, a first aspect of the present invention involves a method for producing a polynucleotide molecule having a defined sequence, comprising the steps of:

(a) incubating a primer having 5' and 3' ends with a template having a 5' region non-complementary to said primer, a 3' region complementary to the 3' end of said primer, and a non-reactive 3' terminus, said template being shorter than said primer, wherein said incubating is conducted under conditions suitable to allow the 3' region of said template to anneal to the primer;

(b) reacting said primer with at least one nucleotide in the presence of a template-dependent polynucleotide polymerase to produce a primer extended at its 3' end by at least one nucleotide complementary to the 5' region of said template;

(c) dissociating the template from the thus-extended primer; and (d) repeating a cycle of steps (a), (b) and (c) for sufficient cycles to obtain a synthesized polynucleotide having a defined sequence, wherein for each cycle (1) the extended primer of step (b) is used as the primer of step (a), (2) the template may be the same as or different from the template of step (a), (3) the template-dependent polynucleotide polymerase may be the same as or different from the template-dependent polynucleotide polymerase of step (a) and (4) the template is shorter than the extended primer.

In various preferred embodiments, the reacting step (b) produces a primer extended at its 3' end by from 1 to 10 nucleotides, more preferably by from 1 to about 6 nucleotides, and in most preferred embodiments, from 1 to about 3 nucleotides, the 3 nucleotides preferably representing a codon. The template of step (a) is from about 10 to about 20 nucleotides in length, and the complementary segment of the template contains from 3 to about 19 nucleotides. The 3' end of the template is rendered non-reactive by the inclusion of a 2',3'-dideoxynucleoside. The non-complementary segment of the template of step (a) and the non-complementary segment of the template of step (d) contain the same number of nucleotides. The primer of step (a) contains from about 20 to about 10,000 nucleotides. The primer may be a vector polynucleotide partially double-stranded or single stranded. In another preferred embodiment, the method further comprises step (e) of reacting a primer extended by at least one reaction cycle of step (d), and more preferably after about 30 such cycles, with a template having a 5' region non-complementary to said primer, a 3' region complementary to the 3' end of said primer, and a reactive 3' terminus, said template being shorter than said primer, wherein step (e) is conducted prior to the sufficient number of cycles to produce the polynucleotide. The step is conducted to accommodate various TDPs that require substantially double stranded templates.

In more preferred embodiments, the template-dependent nucleotide polymerase is a DNA polymerase, and the polynucleotide molecule is a DNA. In most preferred embodiments, the object polynucleotide is a gene or a gene segment.

A second aspect of the present invention is directed to a composition of multiple populations of templates for producing any desired polynucleotide molecule, e.g., a gene, having a defined sequence, in accordance with the first aspect of the present invention. In preferred embodiments, the composition is provided in the form of a kit, wherein each such template population is disposed in a separate container and each of said templates comprises a plurality of non-degenerate nucleotide positions, N, and which may have at least one degenerate nucleotide position, X, wherein the number of template populations ranges from 4 to $4^N$, and the maximum number of templates in each population is $A^X$ wherein A represents 2, 3 or 4. "X" is equal to 2, when for example, only C or T is at the degenerate position rather than all four nucleotides A, G, C and T. Likewise, "X" is equal to three, when only one of three nucleotides is at the degenerate position. In other preferred embodiments, wherein the template composition is used to synthesize a gene having C codons or T nucleotides, the maximum number of template populations is equal to C and T, respectively. In yet other preferred embodiments, the maximum number of template populations is equal to $20^N$. In other preferred embodiments, the maximum number of template populations is $4^M$, wherein "M" represents the highest number of non-degenerate nucleotide positions contained in any one template in the composition.

In other preferred embodiments, the kit contains a grid of wells such that each well contains a single template sequence dissolved in a suitable biological solution such as a buffer. The grid of wells containing templates (i.e., the template library) is comprised of a sufficient number of wells to contain all of the templates required for the synthesis of any defined polynucleotide sequence. The number of wells, Y, is dependent on the total number of nucleotides, Z, contained in each template such that $4^Z \geq Y$. The amount of template solution in each well generally ranges from about 20 µL to about 2000 µL, and the concentration of template generally ranges from about 1 µM to about 1000 µM.

The present invention offers several advantages over state of the art methods. Compared to chemical synthesis methods, the rolling template method provides for greater efficiency of coupling between the growing DNA strand and the added nucleotides, high specificity and low occurrence of side reactions. Therefore, the synthetic polynucleotide need not be chemically treated to deprotect the bases. Consequently, the combination of the aqueous environment in which synthesis may be conducted and the enzymatic processing allows the synthesized polynucleotide to be cloned immediately and eliminates waste-disposal problems. Furthermore, the present invention contains an inherent editing process. Polynucleotide chains which do not receive nucleotides during the synthetic cycle (i.e., failure polynucleotides) will not participate in subsequent cycles due to the absence of a complementary sequence for template annealing. Rapid purification of the full length polynucleotide can thus be accomplished.

The present invention also provides for the direct synthesis of genes or portions thereof onto vector substrates, and thus eliminates the need for another preparative step in cloning processes. The synthesis of the nucleic acids in segments, such as via the addition of one codon (i.e., three nucleotides) per cycle, optimizes the rate of assembly, reduces costs and simplifies post-synthesis purification. Genes having codons optimized for expression in various microorganisms is yet another advantageous feature of the invention. It allows for unlimited mutagenesis in the sense that the complete re-creation of a gene of interest is the ultimate mutagenesis. The method can also be customized for optimal conditions of annealing, extension, and ligation for any given polynucleotide by using sequence data and software.

DETAILED DESCRIPTION OF THE PREFERRED EMBODIMENTS

Figure 1:
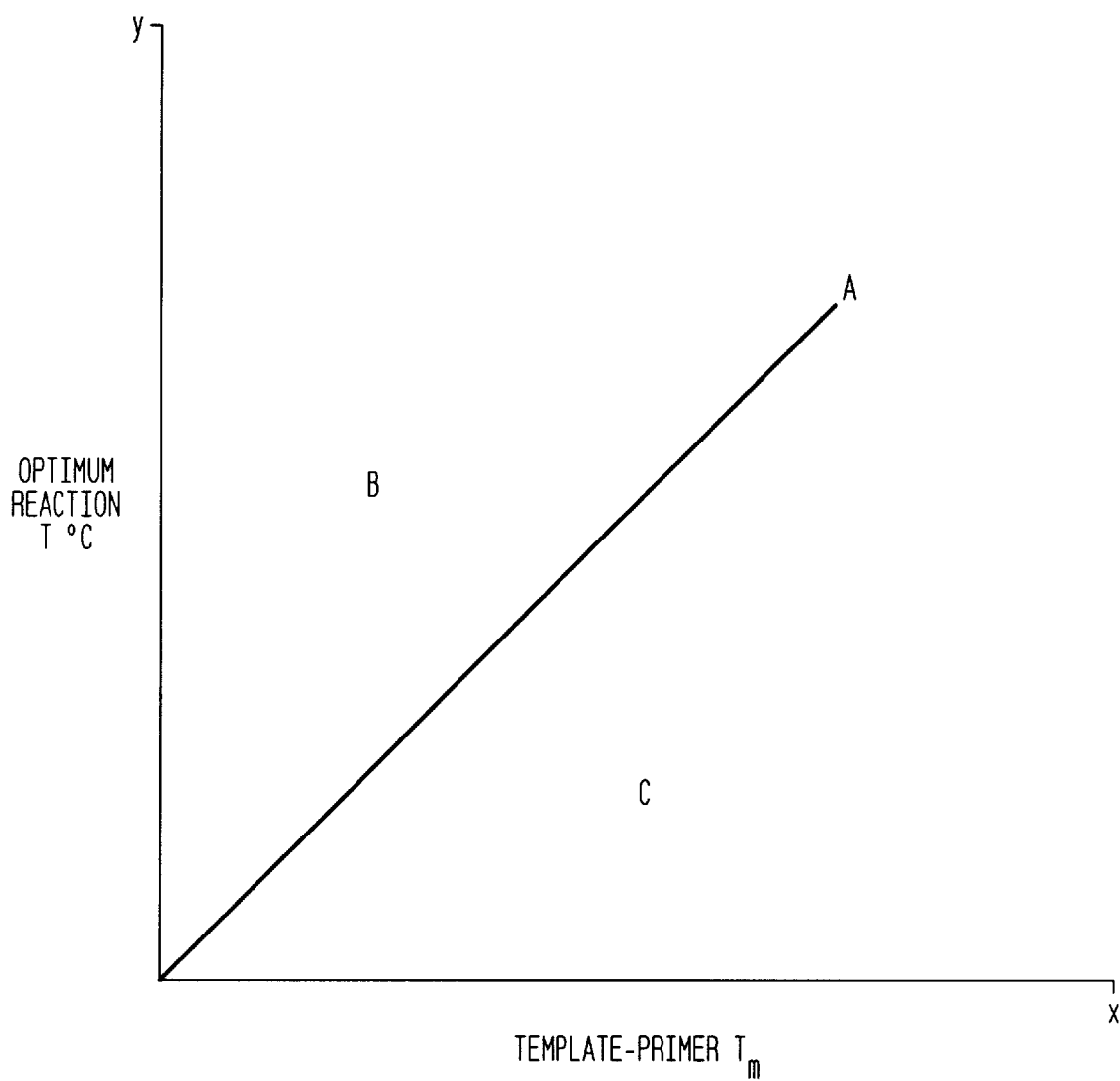
FIG. 1 is a graph illustrating the relationship between the optimal reaction temperature of the given temperature dependent polymerase (y-axis) and the Tm of an annealed primer-template substrate (x-axis).

The present invention provides methods which utilize a plurality of reaction cycles, each involving the reaction of an annealed primer-template substrate with a template dependent polynucleotide polymerase (hereinafter "TDP"), to produce an oligo- or polynucleotide. In each successive cycle, the extended primer of the previous cycle is annealed to a template that directs the addition of specific nucleotide (s) to the growing 3' end of the primer. The templates used in each cycle are selected from a library of templates designed to accommodate the synthesis of polynucleotides of any sequence, or a library customized for a polynucleotide having a specific sequence. The TDPs for each cycle are chosen on the basis of the same factors governing most enzyme-substrate reactions, namely on the basis of the chemical and physical properties of a given primer-template duplex.

The primers of the present invention are typically an oligo- or polynucleotide. The length of the primer typically ranges from about 20 nucleotides to about 10,000 nucleotides. The shorter primers are oligonucleotides that are entirely single stranded or contain one or more double stranded regions and a single stranded region consisting of at least the number of nucleotides contained in the complementary region of the template. An example of a longer primer is a vector polynucleotide. Vector polynucleotides are closed circular DNA molecules capable of autonomous replication in an organism; they typically contain from about 3000 nucleotides to about 20,000 nucleotides. They are commercially available from numerous vendors (e.g. pBS (±) Phagemid Vectors, Stratagene, Inc. catalogue #s 211201 and 211202). Vector polynucleotides may also contain a single stranded region consisting of at least the number of nucleotides contained in the complementary region of the template.

In general, the primers of the present invention are composed of dNTPs, rNTPs, peptide-nucleic acids (PNAs), 2'-O-methyl rNTPs, thiophosphate linkages, additions to the amines of the bases (e.g. linkers to functional groups such as biotin), non-standard bases (e.g. amino-adenine, iso-guanine, iso-cytosine, N-methylformycin, deoxyxanthosine, difluorotoluene), virtual nucleotides (e.g. Clontech products #5300, #5302, #5304, #5306), non-nucleotide components (e.g. Clontech product Nos. 5191, 5192, 5235, 5240, 5236, 5238, 5190, 5225, 5227, 5229, 5223, 5224 and 5222) and combinations thereof. The primers contain reactive 3' hydroxyl groups. They are also longer than the template, both before and after a reaction with a TDP. After reacting with a TDP in the presence of the template, the primer is extended at its 3' end by at least one additional nucleotide, the added nucleotide(s) being complementary to the nucleotide(s) contained in the non-complementary segment of the template.

In general, the templates of the present invention have a compositional nature substantially similar to the primers and contain an oligonucleotide molecule composed of either dNTPs, rNTPs, peptide-nucleic acids (PNAs), 2'-O-methyl rNTPs, thiophosphate linkages, additions to the amines of the bases (e.g. linkers to functional groups such as biotin), non-standard bases (e.g. amino-adenine, iso-guanine, iso-cytosine, N-methylformycin, deoxyxanthosine, difluorotoluene) virtual nucleotides (e.g. Clontech products #5300, #5302, #5304, #5306), or combinations thereof.

The templates of the present invention contain at least two segments, a primer-complementary segment and a primer-non-complementary segment. The template may also contain non-nucleotide spacers that do not serve as binding partners. The segment of the template complementary to the primer generally contains 3 or more complementary bases and includes the 3' region of the template which may or may not include the 3' nucleotide. The primer complementary region may also contain mismatches (i.e., one or mere nucleotides non-complementary to the corresponding nucleotide on the primer) that do not inhibit the template function. For example, the bold mismatch (between the 5' "A" of the primer and the 3' "A" of the template) would not affect the primer extension reaction, particularly in the case of Klenow polymerase:

```
AGCTAGCTAGCT 5'  SEQ ID NO:1 template;

and

ACGATCGATCG 3'  SEQ ID NO:2 primer.
```

To prevent elongation of the template in the 5'-3' direction, the templates are modified to contain non-reactive 3' ends. In a preferred embodiment, 3' reactivity of the template is eliminated by incorporating a 2',3'-dideoxynucleoside at the ultimate 3' position of the template oligonucleotide. As described below, in some instances templates having reactive 3' ends are required to accommodate the substrate specificities of certain TDPs.

The primer non-complementary segment is contained in the 5' region of the template, and includes 1 or more bases, including the 5' nucleotide. The primer non-complementary segment functions as the substrate for the TDP and directs the attachment of the appropriate nucleotide to the 3' end of the primer by the enzyme. As explained in greater detail below, in preferred, embodiments of the present invention, the primer-complementary region contains about 10 nucleotides; in more preferred embodiments, it contains about 6 nucleotides; and in most preferred embodiments, it contains about 3 nucleotides.

The templates of the present invention may contain ligands attached to the 3' end, the 5' end, or both ends, which in addition to eliminating primer activity, may provide other functionalities. Examples of such terminal modifications include incorporation of biotin, acridine, rigamycin, free amine groups, sulfhydryl, fluorescein, trityl, dimethoxytrityl, dideoxynucleotidyl or 3'-deoxy nucleotidyl groups.

In the method of the present invention, the TDPs extend the primer polynucleotide by adding at least one complementary nucleotide only to a 3' hydroxyl adjacent to an unpaired nucleotide on the non-complementary segment of the template. That is, the TDPs add a nucleotide or nucleotides complementary to the nucleotide(s) comprising the 5' end of the template, only to the 3' end of the primer. The nucleotides of the present invention may be unmodified and contain a reactive 3' hydroxyl group, or they may be modified to have ligands attached to the bases (e.g. linkers attached to functional groups such as biotin). The 3' hydroxyl group of the nucleotides may be further modified (e.g., 3' esters or ethers) provided that they do not inhibit phosphodiester bond forming activity. The nucleotides must have a triphosphate at the 5' hydroxyl. The nucleotides may contain non-standard bases such as amino-adenine, iso-guanine, iso-cytosine, N-methylformycin, deoxyxanthosine or difluorotoluene.

The primer-complementary segments of the templates and the primers anneal to form a double stranded structure. As the term is used herein, annealing is the process of positioning two single stranded oligo- or polynucleotide strands relative to each other such that, where possible, hydrogen bonding between C & G and between A & T is maximized and the strands are in anti-parallel orientation to each other. Annealing produces an anti-parallel double stranded oligo- or polynucleotide structure containing a segment or segments of complementary nucleotides. For purposes of the present invention, these double stranded structures can be stable or unstable. A stable double stranded structure maintains hydrogen bonding of the anti-parallel strands for a prolonged time period. An unstable double strand structure maintains the hydrogen bonding relatively briefly. The stability of any double stranded structure is a function of the length and nucleotide composition of the complementary regions of the component single stranded molecules. For example, complementary regions of 50 nucleotides or more are substantially more stable than complementary regions having less than 20 nucleotides. The temperature and pH of the surrounding liquid medium are two additional factors that affect the stability of double strand structures. For instance, at high temperature (e.g., 100° C.) or high pH (e.g., pH 12), all double strand structures are unstable. The temperature at which 50% of any particular oligo- or polynucleotide is in an annealed state with a complementary polynucleotide is referred to as the Tm of the oligo- or polynucleotide. For purposes of the present invention, Tm (in degrees centigrade) can be approximated as follows: (number of purines in polynucleotide×4)+(number of pyrimidines×2); however, other methods can be used (see for example Maniatis et al., supra).

Annealing of two single stranded oligo- or polynucleotide sequences (i.e., the template and primer) is a prerequisite for the creation of a substrate for TDPs. Annealing can be accomplished in a suitable buffer (e.g., 1 M NaCl, 50 mM Tris-Cl, pH 7.6). The concentration of each polynucletoide ranges generally from about 0.1 $\mu$M to about 100 $\mu$M. The solution containing the polynucleotides is heated to Tm+20° C., or to 100° C., for about 5 minutes. The solution is then allowed to cool slowly to the Tm where it is maintained for about 30 minutes. The solution is then allowed to cool slowly to room temperature. The resulting double strand polynucleotide is stably annealed at about 10° C. below Tm. At any temperature above Tm, the double strand structure is unstable.

A variety of TDPs may be used in the methods of the present invention. Examples of commercially available DNA polymerases include E. coli DNA polymerase I and the Klenow fragment of E. coli DNA polymerase I. In preferred embodiments, the TDPs have no 5'-3' or 3'-5' exonuclease activities. Klenow (3'-5' exo-) is one example of such a polymerase. Other useful DNA polymerases are Vent DNA polymerase, Vent (exo-), Deep Vent, Deep vent (exo-), 9° N DNA polymerase, T4 DNA polymerase, T7 DNA polymerase, T7 RNA polymerase, M-MuLV reverse transcriptase, SP6 RNA polymerase, and Taq DNA polymerase. In embodiments wherein the polynucleotide is other than a DNA, suitable polynucleotide TDPs include SP6 and T7 RNA polymerase.

TDPs do not necessarily share the same substrate preferences. Some TDPs require stable double strand substrates whereas others do not require stable double stranded substrates. Thus, the choice of TDP depends mainly on the stability of double strand substrate that is formed in the reaction solution. In a preferred embodiment, unstable double strand template-primer annealed substrates and appropriate TDPs are used. Without intending to be bound by any particular theory of operation, Applicant believes that the instability of the annealed primer-template reaction product that serves as the substrate for the TDP allows for a more efficient exchange of templates after each cycle of the rolling-template primer elongation process. All previous template directed primer extension methods have envisioned double stranded reaction products that are stable. Because such substrate preferences are known in the art, the skilled artisan would be able to select suitable reaction parameters for any given TDP in accordance with standard procedures.

Polymerases having an optimal reaction temperature of 25° C. and requiring a stably annealed template-primer duplex dictate a Tm of the double strand of greater than 25° C. Polymerases with higher optimal reaction temperatures (which also require a stable annealed double strand) will consequently entail longer double strand substrates. Additionally, if a polymerase does not require stable and annealed double strand substrates, then the reaction may be performed at an optimal temperature which is below the Tm of the substrate. FIG. 1 illustrates the linear relationship between the optimal reaction temperature of a given TDP and the Tm of the annealed primer-template substrate. A TDP which has an optimal reaction temperature coinciding with the Tm of its double strand substrate defines line A. These TDPs can utilize an unstable double strand for primer extension. Region B defines polymerases capable of accepting as substrates unstable template-primer duplexes for optimal reaction rates. The double strand substrates of region B are more unstable than those of line A. Region C defines polymerases which require stable double strand substrates for optimal reaction rates.

The molar ratio of primer to template necessary to elicit an optimal reaction rate may vary, and is generally within the range of from about 100:1 to about 1:100. The selection of a given ratio depends on the properties of the TDP catalyzing the reaction. Every TDP has an optimum ratio of template to primer to achieve a maximal reaction rate. This ratio in turn will depend on the requirement of the TDP for double strand substrate stability. Referring again to FIG. 1, TDPs requiring double strand substrates as in category C will require at least an equimolar ratio of template and primer. Polymerases in category B or on line A may catalyze primer extension when the concentration of primer is in excess of the concentration of template.

Practice of the method of the present invention is facilitated by the provision of a pre-prepared composition or library of templates for producing any desired polynucleotide molecule having a defined sequence. The size and complexity of the template library needed for the series of reaction cycles to produce the object polynucleotide are determined mainly by the substrate requirements of the particular polymerase. A polymerase that requires a long template-primer duplex will entail a library of greater complexity than a polymerase requiring a short template-primer duplex. For example, all possible sequences of 10 bases (assuming no degeneracy) will require a library of 1,048,576 members (i.e., $4^{10}$). By contrast, all possible templates of 8 bases require a library of 65,536 members (i.e., $4^8$). Increasing degeneracy of the template sequence will decrease library complexity. A degenerate oligo- or polynucleotide contains more than one nucleotide at a given position. A highly degenerate template, for instance, would contain all four nucleotides (N) at multiple positions. For example, a library containing all possible templates of 10 bases which contain 1 position of complete degeneracy reduces the library number by a factor of 4 and thus requires 262,144 members. The library size would be equal to less than about $X^{Y-z}$, wherein X equals 4, y equals the length of the template, and z equals the number of degenerate positions. A second position of degeneracy in a 10-base template further reduces the library size to 65,536 members.

Polymerases requiring long template-primer duplexes as substrates entail libraries of high complexity, as shown in Table 1.

TABLE 1

Design and Construction of Templates and Template Libraries Useful for De Novo Gene Synthesis

| Configuration (3'–5' direction) | Tm range[1] (degrees centrigrade) | Approximate Complexity | Degeneracy |
|---|---|---|---|
| Unique sequences, variable Tm | | | |
| C5S12 | 10/12–20/24 | 4096 | Unique |
| C6S1 | 12/14–24/28 | 16,384 | Unique |
| C7S1 | 14/16–28/32 | 65,536 | Unique |
| C8S1 | 16/18–32/36 | 262,144 | Unique |
| Degenerate sequences, variable Tm | | | |
| N1C4S1 | 10/12–20/24 | 1024 | 4-fold |
| N1C5S1 | 12/14–24/28 | 4096 | 4-fold |
| N1C6S1 | 14/16–28/32 | 16384 | 4-fold |
| N1C7S1 | 16/18–32/36 | 65536 | 4-fold |
| N2C4S1 | 12/14–24/28 | 1024 | 16-fold |
| N2C5S1 | 14/16–28/32 | 4096 | 16-fold |
| N2C6S1 | 16/18–32/36 | 16384 | 16-fold |
| N2C7S1 | 18/20–36/40 | 65536 | 16-fold |
| N3C4S1 | 14/16–28/32 | 1024 | 64-fold |
| N3C5S1 | 16/18–32/36 | 4096 | 64-fold |
| N3C6S1 | 18/20–36/40 | 16384 | 64-fold |
| N3C7S1 | 20/22–40/44 | 65536 | 64-fold |
| Limited Tm With Variable "C" sequences | | | |
| A. Unique sequences | | | |
| C (10 pyr) S1 | | | |
| C (8 pyr, 1 pur) S1 | | | |
| C (6 pyr, 2 pur) S1 | | | |
| C (4 pyr, 3 pur) S1 | 20/22–24 | 10,000 | Unique |
| C (2 pyr, 4 pur) S1 | | | |
| C (5 pur) S1 | | | |
| B. Degenerate sequences | | | |
| N1C (10 pyr) S1 | | | |
| N1C (8 pyr, 1 pur) S1 | | | |
| N1C (6 pyr, 2 pur) S1 | | | |
| N1C (4 pyr, 3 pur) S1 | 22–24/24–28 | 10,000 | 4-fold |
| N1C (2 pyr, 4 pur) S1 | | | |
| N1C (5 pur) S1 | | | |
| N2C (10 pyr) S1 | | | |
| N2C (8 pyr, 1 pur) S1 | | | |
| N2C (6 pyr, 2 pur) S1 | | | |
| N2C (4 pyr, 3 pur) S1 | 24–28/26–32 | 10,000 | 16-fold |
| N2C (2 pyr, 4 pur) S1 | | | |
| N2C (5 pur) S1 | | | |
| Unique sequences, multiple additions | | | |
| A. 2 Nucleotides | | | |
| C5S2 | 10/14–20/28 | 16,384 | Unique |
| C6S2 | 12/16–24/32 | 65,536 | Unique |
| C7S2 | 14/18–28/36 | 262,144 | Unique |
| C8S2 | 16/20–32/40 | 1,048,576 | Unique |

TABLE 1-continued

Design and Construction of Templates and Template Libraries
Useful for De Novo Gene Synthesis

| Configuration (3'–5' direction) | Tm range[1] (degrees centrigrade) | Approximate Complexity | Degeneracy |
|---|---|---|---|
| B. 3 Nucleotides | | | |
| C5S3 | 10/16–20/32 | 65,536 | Unique |
| C6S3 | 12/18–24/36 | 262,144 | Unique |
| C7S3 | 14/20–28/40 | 1,048,576 | Unique |
| C8S3 | 16/22–32/44 | 4,194,304 | Unique |
| C. Selected Codons (i.e., one codon per amino acid) | | | |
| C6S3 | 10/16–20/32 | 8000 | Unique |
| C9S3 | 12/18–24/36 | 160,000 | Unique |
| Degenerate sequences, multiple additions | | | |
| A. 2 Nucleotides | | | |
| N1C4S2 | 10/14–20/28 | 4,096 | 4-fold |
| N1C5S2 | 12/16–24/32 | 16,384 | 4-fold |
| N1C6S2 | 14/18–28/36 | 65,536 | 4-fold |
| N1C7S2 | 16/20–32/40 | 262,144 | 4-fold |
| B. 3 Nucleotides | | | |
| N1C4S3 | 10/16–20/32 | 16,384 | 4-fold |
| N1C5S3 | 12/18–24/36 | 65,536 | 4-fold |
| N1C6S3 | 14/20–28/40 | 262,144 | 4-fold |
| N1C7S3 | 16/22–32/44 | 1,048,576 | 4-fold |
| C. Selected Codons (i.e., one codon per amino acid) | | | |
| N3C3S3 | 12/16–24/36 | 400 | 64-fold |
| N3C6S3 | 18/24–36/48 | 8,000 | 64-fold |
| N6C3S3 | 18/24–36/48 | 400 | 4096-fold |
| Randomized Additions | | | |
| C6N1 | 12/14–24/28 | 4096 | 4-fold |
| C6N2 | 12/16–24/32 | 4096 | 16-fold |
| C6N3 | 12/18–24/36 | 4096 | 64-fold |
| N1C6N1 | 14/16–28/32 | 4096 | 16-fold |
| N1C6N2 | 14/16–28/36 | 4096 | 64-fold |
| N2C6N1 | 16/18–32/36 | 4096 | 64-fold |
| N2C6N2 | 16/18–32/40 | 4096 | 256-fold |
| N3C6N1 | 18/20–36/40 | 4096 | 256-fold |
| N4C6N1 | 20/22–40/44 | 4096 | 1024-fold |
| N4C6Pyl | 20/22–40/42 | 2048 | 512-fold |
| N4C6Pul | 20/24–40/44 | 2048 | 512-fold |

In Table 1, "pyr" means pyrimidine; and "pur" means purine; "C" means the region or segment of the template that is non-complementary to the primer; "S" means the region or segment of the template that is non-complementary to the primer and which serves as the substrate for the TDP that directs the attachment of the appropriate nucleotide to the 3' end of the primer by the TDP; and "N" denotes a position of degeneracy wherein each one of the four nucleotides is included at that position during the synthesis of the template such that the resulting template population consists of four different sequences in approximately equal abundance.

As a consequence, additional positions containing degeneracy will result in a larger number of template sequences by the formula $4^N$ where N refers to the number of positions of fourfold degeneracy.

Increasing template degeneracy at a constant DNA concentration (wherein DNA concentration is equal to the sum of the amount of template and the amount of primer) will decrease the template/primer molar ratio where the template is considered to be the perfect complement to the primer. At N=1, 25% of the template DNA will be the perfect complement, whereas at N=4, less than 0.4% of the template DNA will be the perfect complement. Referring again to FIG. 1, use of the TDPs of region C will result in suboptimal reaction conditions unless total template DNA in the reaction mix is increased.

The size and complexity of the template library are also determined by the number of nucleotides added to the primer during any one cycle of the reaction. As shown in Table 1, primer extension of two or more nucleotides proportionately increases the complexity of the template library. On the other hand, addition of 3 nucleotides defining a codon, wherein the encoded amino acid is specified by only that single codon (i.e., ATG for Met and TGG for Trp), can be used to limit the complexity of the library. The resulting library of all possible codon combinations (limited to one per amino acid) expands as a multiple of 20 rather than a multiple of 4. See Table 1.

Preferred embodiments contemplate the addition of from 1 to about 10 nucleotides to the primer. In more preferred embodiments, from 1 to about 6 nucleotides are added, and in the most preferred embodiments, from 1 to about 3 nucleotides are added. In embodiments wherein 3 nucleotides are added, it is preferred that they represent a codon. Although embodiments involving the addition of more than about 10 nucleotides are embraced by the present invention, they are less preferred because of the relative size and complexity of the template library that would be required.

Templates comprised of homopolymers will result in continual, unwanted additions to the primer. Thus, when the method of the present invention is used to synthesize a polynucleotide encoding a polypeptide, it is preferred to avoid such homopolymeric subsequences in the template. Suitable alternatives to homopoloymers can be derived from an understanding of the coding frame and/or the amino acid sequence encoded by the object polynucleotide sequence. Homopolymer sequences of DNA encode either polyglycine (GGG . . . ), poly-lysine (AAA . . . ), poly-proline (CCC . . . ), or poly-phenylalanine (TTT . . . In each case, alternative codons can be employed which will interrupt the homopolymer nucleotide sequence leaving the encoded amino acid sequence intact. For glycine, the alternative codons are GGA, GGC, or GGT; for lysine, AAG, for proline, CCA, CCG, or CCT; and for phenylalanine, TTC. Alternatively, in instances where DNA sequences of unknown reading frame are being synthesized, the synthetic segment containing a homopolymer domain can be synthesized in all three reading frames each containing the appropriate codon changes.

In preferred embodiments, the composition of templates is disposed in a grid of wells such that each well contains a single template dissolved in a suitable biological solution such as a buffer. Suitable buffers or solutions include Tris, Hepes, Mops, TEA, Tricine, Pipes and Bis-Tris Propane (Sigma Chemical Co., St. Louis). The grid of wells containing templates (i.e., the template library) is comprised of a sufficient number of wells to contain all of the templates required for the synthesis of any defined polynucleotide sequence. The number of wells, W, is dependent on the number of nucleotides, T, contained in each template such that $4^T \geq W$. The amount of template solution in each well generally ranges from about 20 µL to about 2000 µL, and the concentration of template generally ranges from about 1 µM to about 1000 µM.

Referring to Table 1, above, the number of wells contained in the template library (library complexity) increases with the number of non-degenerate nucleotide positions in the templates. Library complexity can be reduced by incorporating all four nucleotides at any particular position of the template. The additional length may enhance the primer extension reaction of a given polymerase.

In general, the reaction conditions for extending the primer using a TDP involve an appropriate buffering system to maintain a constant pH, a divalent cation, primer polynucleotide, template polynucleotide, nucleotide(s), and enzyme. Additional reagents, such as reducing agents, monovalent cations, or detergents may be added to enhance the reaction rate. Different polymerases may have different optimal pH values or ion concentrations. In the case of Klenow polymerase, for example, reaction conditions are 10 mM Tris-HCl pH 7.5, 5 mM $MgCl_2$, 7.5 mM dithiothreitol, 1 mM nucleotide, 0.1–100 pmol primer, 0.1–100 pmol template, 0.1–10 units Klenow enzyme. A 9° Nm polymerase reaction contains 10 mM KCl, 20 mM TrisCl pH 8.8, 10 mM $(NH_4)_2SO_4$, 2 mM $MgSO_4$, 0.1% Triton X-100, 1 mM nucleotide, 0.1–100 pmol primer, 0.1–100 pmol template, per 0.1–10 units 9° Nm enzyme. M-MuLV reverse transcriptase uses 50 mM Tris-Cl pH 8.3, 8 mM $MgCl_2$, 10 mM dithiothreitol, 1 mM nucleotide, 0.1–100 pmol primer, 0.1–100 pmol template, per 0.1–10 units M-MuLV enzyme. Reactions may vary depending upon the TDP. For example, Klenow polymerase exhibits optimal catalytic activity at 25° C., 9° Nm polymerase at 72°–80° C., and M-MULV reverse transcriptase at 37° C.

After the extension reaction, the template is removed from the now extended primer. Separation of primer from template can be accomplished by any of a variety of methods including gel electrophoresis and column chromatography (which separate DNA fragments on the basis of size) as described in Sambrook et al., *Molecular Cloning: A Laboratory Manual*, Cold Spring Harbor Laboratory, Cold Spring Harbor, N.Y. (1989). Prior to performing the separation, the reaction solution may be heated to (Tm+25° C.) to disrupt any primer-template duplexes.

In a preferred embodiment, the primer strand is attached by its 5' end to a solid support, and the reaction conditions include the support with attached primer, as well as the template and other components. Examples of solid supports include but are not limited to controlled pore glass, cross-linked agarose, polyvinyl chloride and magnetic beads. The primer may be attached to the support covalently or non-covalently. An example of a covalent method is reaction of an amine group located at the 5' end of the primer with N-hydroxy succinimide (NHS) attached to the support. A typical support containing NHS esters is Affi-gel (BioRad Laboratories). Oligonucleotides derivatized to contain 5' amino groups are available commercially (e.g. GenoSys Biotechnologies, Inc.). An example of non-covalent attachment is biotin binding to streptavidin which is immobilized to the support. A typical support containing immobilized streptavidin is streptavidin-agarose (Sigma Chemical Co.). Non-covalent attachment may also be achieved by annealing of the 5' end of the primer to a complementary DNA immobilized by its 3' end to a solid support. The segment annealed should be sufficiently stable to remain annealed during repeated cycles.

As is evident to one of skill in the art, release of synthetic DNA from solid supports can be accomplished by a variety of methods and is dependent on the type of chemical linkage holding the DNA to the support. An ester or an RNA linkage can be released by base; an ether linkage can be released by acid; a disulfide linkage can be released by reducing agents (e.g. mercaptoethanol). Non-covalent attachments (i.e. annealing or streptavidin-biotin) are generally released by heating in an appropriate solution. Annealed segments are released by heating to 100° C. in water; biotinylated segments are released by heating to 110° C. in 7M urea, 0.1% sodium dodecyl sulfate. Enzymatic methods for releasing DNA from supports include ribonucleases for RNA linkers, restriction enzymes for DNA linkers, and proteases for peptide linkers.

After the extension of a primer attached to a solid support, the reaction solution may be heated to (Tm+25)° C. to disrupt any stable annealing. The solid support containing the primer is then removed from reaction liquid and introduced into a new reaction chamber. Separation of support-primer from reaction solution may be by filtration or the support itself may be removed from the liquid and transferred to a new reaction vessel. Prior to introducing the support-primer into a new reaction liquid, it is advisable to immerse the support-primer in a washing solution to insure that no template or polymerase from the previous reaction carries over into the next reaction. Appropriate washing solutions include water at a temperature which is 25° C. above the Tm of the previous template-primer complex, or alkaline solutions such as 0.1 M sodium hydroxide or protein denaturants such as 7 M urea and sodium dodecyl sulfate. If washing is performed in alkaline or denaturing solutions, it is preferred that the support-primer is neutralized and rinsed in an appropriate buffer (e.g. 100 mM Tris-HCl pH 7.5) prior to introduction into the next vessel containing reaction liquid.

The next cycle of synthesis is initiated by introduction of the support-primer (extended from the previous reaction) into a new reaction solution containing appropriate buffers, cations, TDP and the next template in the sequence. In a preferred embodiment, the 3' end of the new template, comprising the primer-complementary portion of its sequence, is identical to the 5' end of the previous template and is the same total length as the previous template. A sequential series of four such templates is shown below as an illustration.

| 1. | 3'dAGCTCAGGTACT | SEQ ID NO:3 | dA addition |
|----|----|----|----|
| 2. | 3'dGCTCAGGTACTA | SEQ ID NO:4 | T addition |
| 3. | 3'dCTCAGGTACTAG | SEQ ID NO:5 | dC addition |

-continued 4.  3'dTCAGGTACTAGC        SEQ ID NO:6    dG addition

If multiple nucleotides (e.g. codons) are to be added at each cycle, the series could be:

1.  3'dCTCAGGTACCTAC  SEQ ID NO:7   T, dA, dG additions 2.  3'dAGGTACTACGCA  SEQ ID NO:8   T, dA, dC additions 3.  3'dTACTACGCATTC  SEQ ID NO:9   dA, dG, additions 4.  3'dTACGCATTCACT  SEQ ID NO:10  T, dA, dG additions For the vast majority of reaction cycles, the templates are modified to contain non-reactive 3' ends to prevent elongation of the template in the 5'-3' direction. Some TDPs, however, prefer or even require a double-stranded primer to be maintained during the reaction cycles. Examples of such TDPs include Klenow exo- and T4 DNA polymerases. Thus, in a further embodiment of the present invention, template fill-in reactions, using templates having reactive 3' ends, are conducted at periodic intervals. In a preferred embodiment, the fill-in reaction is conducted after about every 30 reaction cycles. One approach to maintaining a double stranded primer is illustrated below:

| | | |
|---|---|---|
| Primer | 5'AGCTAGCTAGCTAGCT | SEQ ID NO:11 |
| 1st extension | AGCTAGCTAGCTAGCTA | SEQ ID NO:12 |
| Template | *CGATCGATCGAT | SEQ ID NO:13 |
| | *=3' blocked (e.g. dideoxy) | |
| 30th extention | 5'AGCTAGCTAGCTAGCTAGCTAGCTAGCTAGCTAGCTAGCTAGCT | SEQ ID NO:14 |
| Template | *TCGATCGATCCA- SEQ ID NO:15 | |
| Primer | 5'AGCTAGCTAGCTAGCTAGCTAGCTAGCTAGCTAGCTAGCTAGCT | SEQ ID NO:16 |
| Fill-in template | TCGATCGATCCA | SEQ ID NO:17 |
| React. product | 5'AGCTAGCTAGCTAGCTAGCTAGCTAGCTAGCTAGCTAGCTAGCT TCGATCGATCGATCGATCGATCGATCGATCGA | SEQ ID NO:18 |

Fill-in templates are used much less frequently than forward synthesis templates; nonetheless, their use entails the preparation of a separate library to accomplish fill-in reactions from any possible sequence. The complexity and degeneracy factors that influence the library size for the TDPs apply equally to library of fill-in templates.

The method of the present invention may be applied advantageously to the synthesis of genes or gene segments (which may be ligated to produce the complete gene). For purposes herein, a gene is a polynucleotide, which when introduced into an appropriate organism or in vitro transcription system, enables the transcription of messenger RNA (mRNA). A typical gene encodes an mRNA of approximately 1,000 nucleotides. In a preferred embodiment, synthesis of a segment of a gene or the entire gene is initiated with a primer DNA strand immobilized to a solid support at its 5' end. In another preferred embodiment, the primer strand is comprised of partially double-stranded DNA. Consequently, synthesis of an entire gene may be accomplished relatively efficiently by simultaneously synthesizing segments of the gene followed by their assembly into the full length sequence.

In another preferred embodiment of the present invention, genes are assembled by preparing gene segments in accordance with the rolling template method and then annealing the complementary single stranded regions of the thus-synthesized segments at the appropriate temperatures. All of the gene components may be flanked by single stranded regions having approximately the same Tm, and then assembled and inserted into a vector in one annealing step or in a sequence of annealing steps.

To assemble genes by joining gene segments with each other or with a vector DNA, it is preferred to initiate the assembly process with a first synthetic segment which remains immobilized to its solid support. Annealing of subsequent segments, which have been released from their solid support, can be performed sequentially. Unannealed components are readily removed by washing the solid support between each sequential annealing step. A preferred wash solution is 0.1 M NaCl, 50 mM Tris-Cl, pH 7.6. The synthetic methods of the present invention facilitate this process of gene assembly because the immobilized DNA segment comprising the first synthetic segment need not be protected as would be required after chemical synthesis of the immobilized segment.

Alternatively, complementary regions with different Tm's may be employed wherein the assembly of each segment occurs at different temperatures:

| | | |
|---|---|---|
| A - | 5'GACTGACTGACT3' Tm = ⁻36° C. | SEQ ID NO:19 |
| B - | 5'AGCTAGCTAGCTAGCT3' Tm = ⁻48° C. | SEQ ID NO:20 |
| C - | 3'TCGATCGATCGATCGA5' | SEQ ID NO:21 |
| D - | 3'TGCATGCATGCATGCATGCA5' Tm = ⁻58° C. | SEQ ID NO:22 |
| E - | 5'ACGTACGTACGTACGTACGT3' | SEQ ID NO:23 |
| F - | 5'TCAGTCAGTCAG3' Tm = ⁻36° C. | SEQ ID NO:24 |

The mixture of segments and an appropriate vector is first heated to about 65° C. in a buffered solution (e.g., containing approximately 0.1 M NaCl). As the solution cools, segments D and E will anneal first, followed by B and C. Annealing of segments A and F to complementary ends which may be immobilized to a solid support occurs last.

In yet other preferred embodiments, the templates are immobilized on a suitable support. A template strand is attached to a solid support by a linker, such as a hydrocarbon tether, which does not anneal to the primer strand. The complementary strand which serves to provide a double stranded primer as substrate for the extension reaction, has a higher Tm than either the initial template-primer complex or the template-primer complex after the extension reaction. In this embodiment, the library of templates is synthesized on the appropriate solid support (such as those disclosed above and which may be used to immobilize the primer, e.g., controlled pore glass) and retained on the support. The reaction solution containing primer, nucleotide(s), buffer and enzyme is contacted with the immobilized template to initiate the reaction.

In yet another embodiment, the reaction may be conducted in solution. A template strand is attached to a binding agent such as a biotin molecule, by a linker such as a hydrocarbon tether, which does not anneal to the primer strand. The complementary strand which serves to provide a double stranded primer as substrate for the extension reaction, has a higher Tm than either the initial template-primer complex or the template-primer complex after the extension reaction. In this embodiment, the extension reaction proceeds with all components in solution. It is preferred that all four nucleotides are present in the reaction mixture. The reaction is terminated by removal of the template strand by adsorption to immobilized streptavidin.

The present invention also provides for the introduction of random sequence variations into a defined segment of a gene. For example, introduction of randomness into the CDR regions of an antibody combining site allows for direct synthesis of a novel antibody. The number of randomized positions that can be added is dependent on the characteristics of the TDP. TDPs that do not tolerate mismatches within 6 bases of the complementary 3' segment of the template may be capable of accurately adding 6 randomized nucleotides in a row. TDPs that do not tolerate mismatches within 4 bases of C region complementary may be capable of accurately adding only 4 randomized nucleotides in a row.

The invention will be further described by reference to the following detailed examples. These examples are provided for purposes of illustration only, and are not intended to be limiting as to the scope of the invention described herein, unless otherwise specified.

EXAMPLES

Example 1

Addition of single deoxynucleotide triphosphate to a primer DNA in solution: comparison of annealed and non-annealed templates.

This example illustrates polymerase activity with stable and unstable templates.

a. Template-primer Complexes with Tm>37° C.

A biotinylated oligodeoxynucleotide of 24 bases (sub1: 5' biotin-CATCAGTACTGCTCGAGGAATTCC 3' SEQ ID NO: 25) was used as a primer. The template was a complementary oligodeoxynucleotide of 25 bases (bus2: 5' CGGAATTCCTCGAGCAGTACTGATC 3' SEQ ID NO:26) containing one extra deoxycytosine at the 5' end. The double-stranded product formed by annealing the two oligonucleotides, i.e., a double-stranded complex, had a melting point of approximately 68° C. The annealing reaction consisted of 5 pmol of template bus2 and 5 pmol of primer $sub_1$ combined in a total volume of 20 µL of polymerase buffer (10 mM Tris-HCl pH 7.5, 5 mM $MgCl_2$, 7.5 mM dithiothreitol). The solution was heated to 75° C. for two minutes, then allowed to cool to 25° C. The addition of a single dGTP to the 3' end of the primer was performed in a total volume of 25 µL of polymerase reaction buffer (10 mM Tris-HCl pH 7.4, 5 mM $MgCl_2$, 7.5 mM dithiothreitol, 1 mM dGTP) containing 5 units of Klenow exo-polymerase (New England Biolabs #212) at 37° C. for ten minutes. One unit is defined as the amount of enzyme required to convert ten moles of dNTPs to an acid-insoluble form in 30 minutes at 37° C. under the conditions defined in the New England Biolabs catalogue.

Evaluation of the reaction product was conducted by polyacrylamde gel electrophoresis (PAGE). The composition of the gel was 100 mM Tris, 90 mM boric acid, 1 mM EDTA, 7 M urea and 17.6% acrylamide. Ten µl of 7 M urea, 0.2% SDS were added to the reaction solution, which was then loaded onto the polyacrylamide gel. Electrophoresis was conducted for two hours at 500 V. The DNA was transferred onto nitrocellulose paper by capillary flow using 3 M NaCl and 100 mM Tris-Cl, pH 7.6. The paper was dried at 80° C. for 30 minutes, soaked in TBST (50 mM Tris-Cl pH 7.6, 150 mM NaCl, 0.2% Tween-20) containing 5% w/v non-fat dried milk. The paper was then soaked in TBST containing 1 µg/mL streptavidin-alkaline phosphatase (SAP) at room temperature for 30 minutes. Unbound SAP was rinsed off with TBST; bound SAP was visualized by incubation in 100 mM Tris-Cl pH 9.5, 5 mM $MgCl_2$, 250 µg/mL BCIP and 500 µg/mL NBT.

The results demonstrated an efficient incorporation of the single nucleotide onto the primer DNA using Klenow polymerase.

b. Template-primer Complexes with $T_m$<37° C.

The same protocol was performed as above except for the following changes. The template (bus 3 5' AGGAATTCCT 3' SEQ ID NO:27) contained only nine bases of complementarity with sub 1. The predicted $T_m$ of the bus 3-sub 1 complex was therefore less than 30° C. The added nucleotide triphosphate was TTP. Then annealing step was excluded from the protocol.

The results demonstrated an efficient incorporation of the single nucleotide onto the primer DNA indicating that a stable double stranded complex is not a requirement for enzymatic addition of single nucleotides to the 3' end of a DNA sequence using Klenow exo-polymerase. Similar results are obtained using 9° $N_m$ and Vent (exo-) DNA polymerases (New England Biolabs).

Example 2

Template configurations for addition of nucleotide triphosphates to primer DNA in solution.

This example illustrates polymerase activity with various template configurations. A variety of oligodeoxynucltoitde structures were tested for their ability to act as templates for DNA polymerases. An alternative primer (sub2 5' biotin-AGCATAGGATCGATGCACTCAGTC 3' SEQ ID NO:28) was used in these experiments.

| | | | | |
|---|---|---|---|---|
| 1. | 5' A<u>GACTGAGTG</u> 3' | SEQ ID NO:29 | bus 4 |
| 2. | 5' GA<u>GACTGAGT</u> 3' | SEQ ID NO:30 | bus 5 |
| 3. | 5' CGA<u>GACTGAG</u> 3' | SEQ ID NO:31 | bus 6 |
| 4. | 5' TCGA<u>GACTGA</u> 3' | SEQ ID NO:32 | bus 7 |

The underlined nucleotides are the portion of the template complementary to the sub 2 3' end. The reaction conditions were the same as those described in Example 1a except the added nucleotide triphosphate was TTP. No annealing step was included in the protocol. The reaction products were analyzed as described in Example 1a. The results demonstrated the efficient transfer of TTP to bus 4,5,6 using Klenow exopolymerase. Similar results are obtained using 9° $N_m$ and Vent (exo-) DNA polymerases (New England Biolabs. Less efficient transfer of the nucleotide was observed using bus 7.

Using the same reaction conditions, bus 5,6 and 7 were used as templates for addition of multiple nucleotides to sub 2. Nucleotide triphosphates added to the reaction mix were T&C with bus 5, T,C, & G with bus 6, and T,C,G, & A with bus 7. The results obtained demonstrated in each case an efficient incorporation of multiple nucleotides onto the primer DNA. Minimal complementarity, as in bus 7, can be compensated for by the addition of multiple nucleotides using Klenow exopolymerase. Similar results are obtained using 9° $N_m$ and Vent (exo-) DNA polymerases (New England Biolabs).

In order to minimize the reactivity of the template 3' end, bus 4,5,6,7 were first reacted with terminal deoxynucleotidyl transferase and dideoxy nucleotide triphosphates in order to eliminate the ultimate 3' hydroxyl group. The reaction conditions were as follows:1 mM $CaCl_2$, 0.1 mM DTT, 20 mM potassium cacodylate, pH 6.8, 50 μm dNTP, 2 nmol template and 40 units tDTase (Promega) in a total volume of 25 μL. The reaction was allowed to proceed at 25° C. for 30 minutes. The bus 4 reaction contained dideoxy CTP; the bus 5 reaction contained dideoxy GTP; the bus 6 reaction contained dideoxy TTP; and the bus 7 reaction contained dideoxy GTP. The reactions were terminated by the addition of 10 μL stop solution (7 M urea, 0.1% SDS) and were heated to 75° C. for ten minutes. Four hundred μL water were added and the solution was applied to a Sep-Pak™ column followed by a washing step with 2 mL water. The modified templates were eluted from the column with 1 mL of acetonitrile which was taken to dryness in vacuo. The dried templates were redissolved in 200 μL water and used in separate template extension reactions with multiple nucleotides as described above. The results demonstrated in each case an efficient incorporation of multiple nucleotides onto the primer DNA demonstrating the compatibility of dideoxy templates in the synthetic process using Klenow exopolymerase. Similar results are obtained using 9° $N_m$ and Vent (exo-) DNA polymerases (New England Biolabs).

Example 3

Degenerate Templates and Mismatched Templates

This example illustrates polymerase activity of various template configurations. A variety of degenerate oligodeoxynucleotide structures were tested for their ability to act as templates for DNA polymerases.

| | | | |
|---|---|---|---|
| 1. | T<u>GACTGN</u> | | random 1 |
| 2. | T<u>GACTNN</u> | | random 2 |
| 3. | T<u>GACNNN</u> | | random 3 |
| 4. | T<u>GANNN9</u> | | random 4 |
| 5. | A<u>GACTGN</u>NNNNN | SEQ ID NO:33 | random 5 |
| 6. | TCTCTCG<u>AGANNNN</u> | SEQ ID NO:34 | random 6 |
| 7. | A<u>GACTGN</u>NNNN | SEQ ID NO:35 | random 7 |
| 8. | A<u>GACN</u>NNNNN | SEQ ID NO:36 | random 8 |
| 9. | A<u>GACTGN</u>NNNNN | SEQ ID NO:37 | random 9 |

"N" indicates the inclusion of all four nucleotides at a single position during the synthesis of the template DNA. The underlined nucleotides indicate the positions expected to contain nucleotides complementary to the sub 2 primer.

Primer extension reactions were performed as described in Example 1. In reactions with templates 1–4, dATP was used as the added nucleotide; templates 5–9 used TTP. The reaction products were analyzed by PAGE and blotting as above. The results showed that templates 5, 7, 8 & 9 directed the transfer of TTP to the 3' end of the primer whereas templates 1, 2, 3,4 and 6 were very inefficient. The results suggest a minimal length of DNA for template activity using the Klenow exo-enzyme (i.e., greater than six nucleotides) which can be comprised of a mixed population of oligonucleotides. When comparing lengths of degenerate segments for template activity, template 8 is far less efficient than any of templates 5, 7 and 9, suggesting a minimum length of non-degenerate primer complementarity (i.e., greater than 3) to enable efficient template activity. Similar results are obtained using 9° $N_m$ and Vent (exo-) DNA polymerases (New England Biolabs).

To further explore activity of degerate templates for addition of codons to primer DNA, the following oligonucleotides were synthesized:

| | | | |
|---|---|---|---|
| 1. | ACT<u>GACN</u>NNN | SEQ ID NO:38 | codon 1 |
| 2. | ACT<u>GACN</u>NNNN | SEQ ID NO:39 | codon 2 |
| 3. | ACT<u>GACN</u>NNNNN | SEQ ID NO:40 | codon 3 |
| 4. | ACT<u>GACTGN</u>NNN | SEQ ID NO:41 | codon 4 |
| 5. | TCA<u>GACTGAN</u>NNNNNN | SEQ ID NO:42 | codon 5 |
| 6. | TCA<u>GACTGAN</u>NNNNN | SEQ ID NO:43 | codon 6 |
| 7. | TCA<u>GACTGAN</u>NNNN | SEQ ID NO:44 | codon 7 |

"N" indicates the inclusion of all four nucleotides at a single position during the synthesis of the template DNA. The underlined nucleotides indicate the positions expected to be complementary to the sub2 primer. Primer extension reactions were performed as described in Example 1. All of the templates used dATP, dGTP, and TTp as the added nucleotides. The reaction products were analyzed by PAGE and blotting as above. The results demonstrated that all templates could direct the addition of a codon to the sub 2 primer, although codon 1 was far less efficient than the others. similar results are obtained using Klenow exo-. 9° $N_m$ and Vent (exo-) DNA polymerases (New England Biolabs).

The effect on primer extension of specific mismatches introduced into the primer template complex was investigated with the following templates:

| 1. | CAACTGAGTG | SEQ ID NO:45 | mismatch 1 |
|---|---|---|---|
| 2. | CGGCTGAGTG | SEQ ID NO:46 | mismatch 2 |
| 3. | CGATTGAGTG | SEQ ID NO:47 | mismatch 3 |
| 4. | CGACCGAGTG | SEQ ID NO:48 | mismatch 4 |
| 5. | CGACTAAGTG | SEQ ID NO:49 | mismatch 5 |

The underlined nucleotides indicate the positions of complementarity to the sub 2 primer. The bold nucleotide in each template is a mismatch (non-complementary nucleotide) with sub 2 when the other nucleotides are in their complimentary positions. Primer extension reactions were performed as described in Example 1. All of the templates used dGTP as the added nucleotide. The reaction products were analyzed by PAGE and blotting as above. The results demonstrate that all of the templates directed the addition of dGTP to the primer 3' end, although mismatch 1, 2 and 3 were far less efficient than mismatch 4 and 5. Similar results are obtained using Klenow exo-. 9° $N_m$ and Vent (exo-) DNA polymerases (New England Biolabs).

Example 4

Primer Immobilization Strategies for Solid Phase DNA Synthesis

This example illustrates polymerase activity using immobilized primers and various primers.

a. Streptavidn Covalently Linked to Plastic.

CovaLinkNH™ immunomodules (Nunc) were used as the polystyrene solid phase for attachment of streptavidin. The polystyrene surface of each well is modified to contain free amino groups. the following solutions were prepared for linking steptavidin to the CovLinkNH™ surface: streptavidin stock solution—1 mg streptavidin, 0.2 mL water, 0.3 mL dimethylsulfoxide; streptavidin/NHS—100 µL streptavidin stock solution, 0.4 mg N-hydroxysulfosuccinimide, 2 mL water; EDC solution—2.46 mg 1-ethyl-3-(3-dimethylaminpropyl)carbodiimide-HCl. Fifty µL of streptavidin-NHS were added to each well of the immunomodule; the linking reaction was started by the addition of 50 µL of EDC solution to each well. The reaction was allowed to proceed at room temperature for two hours. The wells were then washed three times with 200 µL TBST (50 mM Tris-HCl, pH 7.6, 150 mM NaCl, 0.1% Tween-20). Binding of a primer containing biotin at the 5' end was performed as follows. Fifty (50) µL TBST containing 2.5 pmol primer were added to each well. Binding was allowed to proceed at room temperature for 30 minutes. Release of the primer for PAGE analysis was effected by the addition of 50 µl of 7M urea/0.1% SDS to each reaction well. The wells were wrapped in two layers off aluminum foil and heated to 110° for 15 minutes. The urea/SDS was then loaded directly onto the gel for PAGE as described above.

b. Primer DNA Covalently Linked to Plastic.

NucleoLink™ Strips (Nunc) were used as the solid phase for attachment of primer DNA. Seventy-five µL of freshly made 10 mM 1-methyl-imidazole, pH 7.0, containing 100 ng of 5'-phosphorylated primer were added to each well. The reaction was started by the addition of 25 µL freshly made 40 mM 1-ethyl-3-(3-dimeehylaminopropyl)carbodiimide dissolved in 10 mM 1-methyl-imidazole, pH 7.0. The strips were incubated at 50° C. for five hours, then washed three times with excess 0.4 M NaOH, 0.25% Tween-20 at 50° C., the strips were washed three times with TBST. Release of the primer for PAGE analysis was conducted by restriction digestion. This technique requires that the primer contain a recognition sequence for a restriction enzyme and that a complementary oligonucleotide is annealed to the primer to create the double stranded DNA necessary for restriction enzyme digestion. The primer sequence (phos 1) was 5' phosphate-TATGGATCCTC-biotin-ATGCACTCAGTC 3' SEQ ID NO:50, where "phosphate" indicates phosphorylation of the 5' hydroxyl group and biotin was incorporated as a virtual nucleotide linker (Clontech #5300; biotin-VN™). The complementary oligonucleotide was 5' ATAGATCTC-GAGGATCCATA 3' SEQ ID NO:51. The oligonucleotides (100 ng of each in each well) were annealed by first heating to 65° C. in 50 µL 150 mM NaCl, 10 mM Tris-HCl, pH 7.9, 10 mM $MgCl_2$. The solution was allowed to cool to room temperature. Twenty units of BamH1 restriction enzyme were then added and the reaction was allowed to proceed for 30 minutes at 37° C. The solution was then loaded directly onto the gel for PAGE as described above.

c. Addition of Nucleotides to Immobilized Primers.

All of the primer extension reactions described in Examples 1–3 were repeated with primers immobilized by one or both of the strategies described above. The reaction products were analyzed by PAGE and blotting as above. The results are summarized below:

| Primer | Mode[1] | Efficient templates | Inefficient templates |
|---|---|---|---|
| sub 1 | mono | bus 2 | |
| sub 1 | mono | bus 3 | |
| sub 2/phos1 | mono | bus 4 | |
| sub 2/phos1 | mono | bus 5 | |
| sub 2/phos1 | mono | bus 6 | |
| sub 2/phos1 | mono | | bus 7 |
| sub 2/phos1 | multi | bus 5 | |
| sub 2/phos1 | multi | bus 6 | |
| sub 2/phos1 | multi | bus 7 | |
| sub 2/phos1 | mono | dd-bus 4[2] | |
| sub 2/phos1 | multi | dd-bus 5 | |
| sub 2/phos1 | multi | dd-bus 6 | |
| sub 2/phos1 | multi | dd-bus 7 | |
| sub 2/phos1 | mono | | random 1 |
| sub 2/phos1 | mono | | random 2 |
| sub 2/phos1 | mono | | random 3 |
| sub 2/phos1 | mono | | random 4 |
| sub 2/phos1 | mono | random 5 | |
| sub 2/phos1 | mono | | random 6 |
| sub 2/phos1 | mono | random 7 | |
| sub 2/phos1 | mono | | random 8 |
| sub 2/phos1 | mono | random 9 | |
| sub 2/phos1 | multi | | codon 1 |
| sub 2/phos1 | multi | codon 2 | |

-continued

| Primer | Mode[1] | Efficient templates | Inefficient templates |
|---|---|---|---|
| sub 2/phos1 | multi | codon 3 | |
| sub 2/phos1 | multi | codon 4 | |
| sub 2/phos1 | multi | codon 5 | |
| sub 2/phos1 | multi | codon 6 | |
| sub 2/phos1 | multi | codon 7 | |
| sub 2/phos1 | mono | | mismatch 1 |
| sub 2/phos1 | mono | | mismatch 2 |
| sub 2/phos1 | mono | | mismatch 3 |
| sub 2/phos1 | mono | mismatch 4 | |
| sub 2/phos1 | mono | mismatch 5 | |

"Mono" mode refers to the addition of single nucleotides in the extension reactions; "multi" refers to the addition of two or more nucleotides; and "dd" refers to addition of a dideoxy nucleotide to the 3' end of the template. The results demonstrate that all of the templates could direct the addition of appropriate nucleotides to immobilized primers. Similar results are obtained using 9° $N_m$ and Vent (exo-) DNA polymerases (New England Biolabs).

Example 5

Repetitive Addition of Codons to a Primer: Self-editing DNA Synthesis.

This example illustrates the self-editing properties of the synthesis system. The following primer (gene 1), immobilized to polystyrene by the method of Example 4a, was used for repetitive codon additions;

gene 1 5' biotin-ATGGATCCTCGAGATCTATGAAG 3' SEQ ID NO:52

A series of overlapping oligonucleotides were used as templates (reading 3'–5'):

| codon 8  | AGATACTTCTTGACA | SEQ ID NO:53 |
| codon 9  | TACTTCTTGACGTTT | SEQ ID NO:54 |
| codon 10 | TTCTTGACGGAGCTC | SEQ ID NO:55 |
| codon 11 | TTGACGGAGGAGTCT | SEQ ID NO:56 |
| codon 12 | ACGGAGGAGAAGTTC | SEQ ID NO:57 |
| codon 13 | GAGGAGAAGACCGTT | SEQ ID NO:58 |
| codon 14 | GAGAAGACCCCTGAG | SEQ ID NO:59 |
| codon 15 | AAGACCCCTCACTGT | SEQ ID NO:60 |
| codon 16 | ACCCCTCACGAGTCC | SEQ ID NO:61 |
| codon 17 | CCTCACGAGCGATTT | SEQ ID NO:62 |

The underlined portion of codon 8 is complementary to the 3' end of gene 1. Codon 9 is complementary to gene 1 containing the additional codon specified by codon 8, and so forth. The bold portion indicates the codon to be added at every step. These templates also include three additional nucleotides at the 5' end which are not utilized for primer extension because their complementary nucleotide triphosphates were not included in the extension reactions. The additional 5' nucleotides are intended to enhance the efficiency of the extension reaction following the observations made in Example 2. Addition of codons to the 3' end of the primer was performed in a total volume of 50 μL of polymerase reaction buffer (10 mM Tris-HCl pH 7.5, 5 mM $MgCl_2$, 7.5 mM dithiothreitol, 1 mM dNTP) containing 2.5 pmol gene 1 primer, 5 pmol template DNA, and 5 units of Klenow exo-polymerase (New England Biolabs #212) at 37° C. for 10 minutes. After each reaction, the reactants were removed and the well was rinsed with water. The final reaction produce was analyzed by PAGE and blotting as above. The results demonstrate the de novo synthesis of a new strand of DNA containing 30 nucleotides (AACTGCCTCCTCTTCTGGGGAGTGCTCGCT) SEQ ID NO:63, attached to the gene 1 primer. The overall efficiency of the series for reactions allowed the observation of the final product. Some of the intermediate reaction products, which represent primers not converted to longer products in the extension reactions, could be observed. Similar results are obtained using 9° $N_m$ and Vent (exo-) DNA polymerases (New England Biolabs).

To explore whether failure sequences of one reaction were substrates of subsequent reactions, the same series of template dependent extensions was repeated in four segments. Segment 1: codon 8 alone; segment 2: codon 8–10; segment 3: codon 8–14; segment 4: codon 8–17. Reactions were performed as above except reactions containing codons 8, 10 or 14 were for only 30 seconds resulting in the introduction of readily observable failure sequences detected after PAGE and blotting. The segment 1 reaction yielded approximately equal amounts of unmodified gene 1 primer as well as gene 1 primer with additional nucleotides (single, double, and triple additions). The unmodified gene 1 primer was observed in segments 2, 3, and 4 in the same abundance as segment 1. Similarly, a prominent failure sequence (unmodified primer) was observed at the 10 and 14 positions, both of which persisted to the end of the reaction series. The results demonstrate that unmodified primers are not subsequently used as substrates with non-complementary primers. Similar results are obtained using 9° Nm and Vent (exo-) DNA polymerases (New England Biolabs).

Example 6

Synthesis and Mutagenesis of an Immunoglobulin Light Chain Variable Region

This example illustrates synthesis and mutagenesis of a polynucleotide encoding an immunoglobulin light chain variable region.

A. Synthesis A primer (kappa) (5' biotin-GACATTGTGATG 3') SEQ ID NO:64 immobilized to streptavidin by the method of Example 4a, is used to initiate the synthesis of the variable region of the light chain of a mouse monoclonal antibody (6A4, Marget et al., Gene 74:335–345 (1988) specific for Pseudomonas aeruginosa membrane protein 1. The nucleotide sequence of the 6A4 variable region and corresponding amino acid sequence SEQ ID NO: 66 are as follows:

```
5'GAC ATT GTG ATG TCA CAG TCT CCA TCC TCC CTG GCT GTG TCA GCA GGA   SEQ ID NO:65
GAG AAG GTC ACT ATG AGC TGC AAA TCC AGT CAG AGT CTG CTC AAC AGT
ATA ACC CGA AAG AAC TTC TTG GCT TGG TAC CAG CAG AAA CCA GGG CAG
TCT CCT AAA CTG CTG ATC TAC TGG GCA TCC ACT AGG GAA TCT GGG GTC
CCT GAT CGC TTC ACA GGC AGT GGA TCT GGG ACA GAT TTC ACT CTC ACC
ATC AGC AGT GTG CAG GCT GAA GAC CTG GCA GTT TAT TAC TGC AAG CAA
TCT TAT AAT CTT CGG ACG TTC GGT GGA GGC ACC AAG CTG GAA ATC AAA
CGG GCT3'
```

The following set of templates (reading 3'–5') is used sequentially to direct the synthesis of the variable region codons. Each template is terminated at its 3' end by a dideoxynucleoside. N refers to a position of four-fold degeneracy in the template sequence.

| # | Sequence | SEQ ID |
|---|---|---|
| 1. | NNNCACTACAGT | SEQ ID NO:67 |
| 2. | NNNTACAGTGTC | SEQ ID NO:68 |
| 3. | NNNAGTGTCAGA | SEQ ID NO:69 |
| 4. | NNNGTCAGAGGT | SEQ ID NO:70 |
| 5. | NNNAGAGGTAGG | SEQ ID NO:71 |
| 6. | NNNGGTAGGAGG | SEQ ID NO:72 |
| 7. | NNNAGGAGGGAC | SEQ ID NO:73 |
| 8. | NNNAGGGACCGA | SEQ ID NO:74 |
| 9. | NNNGACCGACAC | SEQ ID NO:75 |
| 10. | NNNCGACACAGT | SEQ ID NO:76 |
| 11. | NNNCACAGTCGT | SEQ ID NO:77 |
| 12. | NNNAGTCGTCCT | SEQ ID NO:78 |
| 13. | NNNCGTCCTCTC | SEQ ID NO:79 |
| 14. | NNNCCTCTCTTC | SEQ ID NO:80 |
| 15. | NNNCTCTTCCAG | SEQ ID NO:81 |
| 16. | NNNTTCCAGTGA | SEQ ID NO:82 |
| 17. | NNNCAGTGATAC | SEQ ID NO:83 |
| 18. | NNNTGATACTCG | SEQ ID NO:84 |
| 19. | NNNTACTCGACG | SEQ ID NO:85 |
| 20. | NNNTCGACGTTT | SEQ ID NO:86 |
| 21. | NNNACGTTTAGG | SEQ ID NO:87 |
| 22. | NNNTTTAGGTCA | SEQ ID NO:88 |
| 23. | NNNAGGTCAGTC | SEQ ID NO:89 |
| 24. | NNNTCAGTCTCA | SEQ ID NO:90 |
| 25. | NNNGTCTCAGAC | SEQ ID NO:91 |
| 26. | NNNTCAGACGAG | SEQ ID NO:92 |
| 27. | NNNGACGAGTTG | SEQ ID NO:93 |
| 28. | NNNGAGTTGTCA | SEQ ID NO:94 |
| 29. | NNNTTGTCATAT | SEQ ID NO:95 |
| 30. | NNNTCATATTGG | SEQ ID NO:96 |
| 31. | NNNTATTGGGCT | SEQ ID NO:97 |
| 32. | NNNTGGGCTTTC | SEQ ID NO:98 |
| 33. | NNNGCTTTCTTG | SEQ ID NO:99 |
| 34. | NNNTTCTTGAAG | SEQ ID NO:100 |
| 35. | NNNTTGAAGAAC | SEQ ID NO:101 |
| 36. | NNNAAGAACCGA | SEQ ID NO:102 |
| 37. | NNNAACCGAACC | SEQ ID NO:103 |
| 38. | NNNCGAACCATG | SEQ ID NO:104 |
| 39. | NNNACCATGGTC | SEQ ID NO:105 |
| 40. | NNNATGGTCGTC | SEQ ID NO:106 |
| 41. | NNNGTCGTCTTT | SEQ ID NO:107 |
| 42. | NNNGTCTTTGGT | SEQ ID NO:108 |
| 43. | NNNTTTGGTCCC | SEQ ID NO:109 |
| 44. | NNNGGTCCCGTC | SEQ ID NO:110 |
| 45. | NNNCCCGTCAGA | SEQ ID NO:111 |
| 46. | NNNGTCAGAGGA | SEQ ID NO:112 |
| 47. | NNNAGAGGATTT | SEQ ID NO:113 |
| 48. | NNNGGATTTGAC | SEQ ID NO:114 |
| 49. | NNNTTTGACGAC | SEQ ID NO:115 |
| 50. | NNNGACGACTAG | SEQ ID NO:116 |
| 51. | NNNGACTAGATG | SEQ ID NO:117 |
| 52. | NNNTAGATGACC | SEQ ID NO:118 |
| 53. | NNNATGACCCGT | SEQ ID NO:119 |
| 54. | NNNACCCGTAGG | SEQ ID NO:120 |
| 55. | NNNCGTAGGTGA | SEQ ID NO:121 |
| 56. | NNNAGGTGATCC | SEQ ID NO:122 |
| 57. | NNNTGATCCCTT | SEQ ID NO:123 |

| | | |
|---|---|---|
| 58. | NNNTCCCTTAGA | SEQ ID NO:124 |
| 59. | NNNCTTAGACCC | SEQ ID NO:125 |
| 60. | NNNAGACCCCAG | SEQ ID NO:126 |
| 61. | NNNCCCCAGGGA | SEQ ID NO:127 |
| 62. | NNNCAGGGACTA | SEQ ID NO:128 |
| 63. | NNNGGACTAGCG | SEQ ID NO:129 |
| 64. | NNNCTAGCGAAG | SEQ ID NO:130 |
| 65. | NNNGCGAAGTGT | SEQ ID NO:131 |
| 66. | NNNAAGTGTCCG | SEQ ID NO:132 |
| 67. | NNNTGTCCGTCA | SEQ ID NO:133 |
| 68. | NNNCCGTCACCT | SEQ ID NO:134 |
| 69. | NNNTCACCTAGA | SEQ ID NO:135 |
| 70. | NNNCCTAGACCC | SEQ ID NO:136 |
| 71. | NNNAGACCCTGT | SEQ ID NO:137 |
| 72. | NNNCCCTGTCTA | SEQ ID NO:138 |
| 73. | NNNTGTCTAAAG | SEQ ID NO:139 |
| 74. | NNNCTAAAGTGA | SEQ ID NO:140 |
| 75. | NNNAAGTGAGAG | SEQ ID NO:141 |
| 76. | NNNTGAGAGTGG | SEQ ID NO:142 |
| 77. | NNNGAGTGGTAG | SEQ ID NO:143 |
| 78. | NNNTGGTAGTCG | SEQ ID NO:144 |
| 79. | NNNTAGTCGTCA | SEQ ID NO:145 |
| 80. | NNNTCGTCACAC | SEQ ID NO:146 |
| 81. | NNNTCACACGTC | SEQ ID NO:147 |
| 82. | NNNCACGTCCGA | SEQ ID NO:148 |
| 83. | NNNGTCCGACTT | SEQ ID NO:149 |
| 84. | NNNCGACTTCTG | SEQ ID NO:150 |
| 85. | NNNCTTCTGGAC | SEQ ID NO:151 |
| 86. | NNNCTGGACCGT | SEQ ID NO:152 |
| 87. | NNNGACCGTCAA | SEQ ID NO:153 |
| 88. | NNNCGTCAAATA | SEQ ID NO:154 |
| 89. | NNNCAAATAATG | SEQ ID NO:155 |
| 90. | NNNATAATGACG | SEQ ID NO:156 |
| 91. | NNNATGACGTTC | SEQ ID NO:157 |
| 92. | NNNACGTTCGTT | SEQ ID NO:158 |
| 93. | NNNTCGTTAGA | SEQ ID NO:159 |
| 94. | NNNGTTAGAATA | SEQ ID NO:160 |
| 95. | NNNAGAATATTA | SEQ ID NO:161 |
| 96. | NNNATATTAGAA | SEQ ID NO:162 |
| 97. | NNNTTAGAAGCC | SEQ ID NO:163 |
| 98. | NNNGAAGCCTGC | SEQ ID NO:164 |
| 99. | NNNGCCTGCAAG | SEQ ID NO:165 |
| 100. | NNNTGCAAGCCA | SEQ ID NO:166 |
| 101. | NNNAAGCCACCT | SEQ ID NO:167 |
| 102. | NNNCCACCTCCG | SEQ ID NO:168 |
| 103. | NNNCCTCCGTGG | SEQ ID NO:169 |
| 104. | NNNCCGTGGTTC | SEQ ID NO:170 |
| 105. | NNNTGGTTCGAC | SEQ ID NO:171 |
| 106. | NNNTTCGACCTT | SEQ ID NO:172 |
| 107. | NNNGACCTTTAG | SEQ ID NO:173 |
| 108. | NNNCTTTAGTTT | SEQ ID NO:174 |
| 109. | NNNTAGTTTGCC | SEQ ID NO:175 |
| 110. | NNNTTTGCCCGA | SEQ ID NO:176 |

Additions of codons to the 3' end of the primer are performed in a total volume of 50 µL of polymerase reaction buffer (10 mM Tris-HCl pH 7.5, 5 mM $MgCl_2$, 7.5 mM dithiothreitol, 1 mM dNTP) containing 2.5 pmol kappa primer, 5 pmol template DNA, 5 units of Klenow exo- polymerase (New England Biolabs #212) at 37° C. for two minutes. After each reaction, the reactants are removed and the well is rinsed with water. The final reaction product is analyzed by PAGE and blotting as above. The results demonstrate the de novo synthesis of the variable region of an immunoglobin light chain gene.

Similar results are obtained using 9° $N_m$ and Vent (exo-) DNA polymerases (New England Biolabs).

B. Mutagenesis The Kappa variable region is re-synthesized as above utilizing a modified set of sequential templates intended to introduce mutations into the three CDR regions during synthesis. The mutagenic templates are as follows:

| | | |
|---|---|---|
| 23. | NNNAGGTCACTT | SEQ ID NO:177 |
| 24. | NNNTCAGTTCCG | SEQ ID NO:178 |
| 25. | NNNCTTCCGGAC | SEQ ID NO:179 |
| 26. | NNNCCGGACGAG | SEQ ID NO:180 |
| 52. | NNNTAGATGAAA | SEQ ID NO:181 |
| 53. | NNNATGAAACGT | SEQ ID NO:182 |
| 54. | NNNAAACGTAGG | SEQ ID NO:183 |
| 91. | NNNATGACGGTA | SEQ ID NO:184 |
| 92. | NNNACGGTATTA | SEQ ID NO:185 |
| 93. | NNNGTATTAAGA | SEQ ID NO:186 |
| 94. | NNNTTAAGAATA | SEQ ID NO:187 |

The newly synthesized kappa variable region contains 10 nucleotide mutations and encodes 5 amino acid changes in the open reading frame, as set forth below (new codons set forth in lower case):

```
5'GAC ATT GTG ATG TCA CAG TCT CCA TCC TCC CTG GCT GTG TCA GCA GGA    SEQ ID NO:188

GAG AAG GTC ACT ATG AGC TGC AAA TCC AGT CAG AGT CTG CTC AAC AGT

ATA ACC CGA AAG AAC TTC TTG GCT TGG TAC CAG CAG AAA CCA GGG CAG

TCT CCT AAA CTG CTG ATC TAC TGG GCA TCC ACT AGG GAA TCT GGG GTC

CCT GAT CGC TTC ACA GGC AGT GGA TCT GGG ACA GAT TTC ACT CTC ACC

ATC AGC AGT GTG CAG GCT GAA GAC CTG GCA GTT TAT TAC TGC cat aat

TCT TAT AAT CTT CGG ACG TTC GGT GGA GGC ACC AAG CTG GAA ATC AAA

CGG GCT3'
```

All patent and non-patent publications cited in this specification are indicative of the level of skill of those skilled in the art to which this invention pertains. All these publications and patent applications are herein incorporated by reference to the same extent as if each individual publication or patent application was specifically and individually indicated to be incorporated by reference.

What is claimed is:

1. A method for synthesizing a polynucleotide molecule having a defined sequence, comprising repeatedly performing a cycle of steps:
   (a) annealing a primer having 5' and 3' ends with a template having a 5' region non-complementary to t he primer, a 3' region complementary to the 3' end of the primer, and a non-reactive 3' terminus, the template being shorter than the primer;
   (b) reacting the primer with at least one nucleotide in the presence of a template-dependent polynucleotide polymerase to produce an extended primer including at its 3' end at least one nucleotide complementary to the 5' region of the template; and
   (c) dissociating the template from the extended primer;
      wherein for each repetition of the cycle the extended primer of step (c) is used as the primer for a next repetition of step (a), the template may be the same as or different from a template of a previous repetition, and the template dependent polynucleotide polymerase may be the same as or different from a template dependent polynucleotide polymerase of a previous repetition.

2. The method of claim 1 wherein a template of a repetition of step (a) has a 5' region containing from 1 to about 10 nucleotides and a primer of step (a) of the same repetition is extended by an equal number of complementary nucleotides.

3. The method of claim 1 wherein a template of a repetition of step (a) has a 5' region containing from 1 to about 6 nucleotides and a primer of step (a) of the same repetition is extended by an equal number of complementary nucleotides.

4. The method of claim 1 wherein a template of a repetition of step (a) has a 5' region containing from 1 to about 3 nucleotides and a primer of step (a) of the same repetition is extended by an equal number of complementary nucleotides.

5. The method of claim 1 wherein a template of a repetition of step (a) has a 5' region containing 3 nucleotides and a primer of step (a) of the same repetition is extended is extended by 3 complementary nucleotide.

6. The method of claim 5 wherein said 3 complementary nucleotides represent a codon.

7. The method of claim 1 wherein a template of a repetition of step (a) has a 5' region containing 1 nucleotide and a primer of step (a) of the same repetition is extended by 1' complementary nucleotides.

8. The method of claim 1 wherein a template of a repetition of step (a) is from about 10 to about 20 nucleotides in length.

9. The method of claim 1 wherein a template of a repetition of step (a) has a 3' region containing from 3 to about 19 nucleotides.

10. The method of claim 1 wherein the non-reactive 3' terminus of a template of a repetition of step (a) comprises a 2',3'-dideoxynucleoside.

11. The method of claim 1 wherein a template of a repetition of step (a) and a template of the next repetition of step (a) each has a 5' region containing the same number of nucleotides.

12. The method of claim 1 wherein a primer of a repetition of step (a) contains from about 12 to about 10,000 nucleotides.

13. The method of claim 1 wherein a primer of a repetition of step (a) comprises a vector polynucleotide.

14. The method of claim 1 wherein a primer of a repetition of step (a) is partially double-stranded.

15. The method of claim 1 wherein a primer of a repetition of step (a) is attached to a solid support.

16. The method of claim 1 wherein said synthesized polynucleotide is a DNA molecule.

17. The method of claim 16 wherein said synthesized polynucleotide is a DNA molecule complementary to a nucleic acid molecule, or a portion thereof, of interest.

18. The method of claim 1 wherein said synthesized polynucleotide is a gene or a gene segment.

19. A method for synthesizing a polynucleotide molecule having a defined sequence, comprising repeatedly performing a cycle of steps:
   (a) annealing a primer having 5' and 3' ends with a template having a 5' region non-complementary to the primer, a 3' region complementary to the 3' end of the primer, wherein the template is shorter than the primer;
   (b) reacting the primer with at least one nucleotide in the presence of a template-dependent polynucleotide polymerase to produce an extended primer including at its 3' end at least one nucleotide complementary to the 5' region of the template; and
   (c) dissociating the template from the extended primer;
      wherein for each repetition of the cycle the extended primer of step (c) is used as the primer for a next repetition of step (a), the template may be the same as or different from a template of a previous repetition, and the template dependent polynucleotide polymerase may be the same as or different from a template dependent polynucleotide polymerase of previous repetition.

20. The method of claim 19 wherein a template of a repetition of step (a) of said cycle has a reactive 3' terminus and a template dependent polynucleotide polymerase of step (b) of said repetition has specificity for a substantially double standard substrate, and wherein a template of all other repetitions of step (a), including a last repetition of step (a) of said cycle has a non-reactive 3' terminus.

21. A method for synthesizing a gene having a defined sequence, or a segment thereof, comprising repeatedly performing a cycle of steps including:
 (a) annealing a primer having 5' and 3' ends with a template having a 5' region non-complementary to the primer, a 3' region complementary to the 3' end of the primer, the template being shorter than the primer;
 (b) reacting the primer with at least one nucleotide in the presence of a template-dependent DNA polymerase to produce an extended primer including at its 3' end at least one nucleotide complementary to the 5' region of the template; and
 (c) dissociating the template from the extended primer; wherein for each repetition of the cycle the extended primer of (c) is used as the primer for the next repetition of step (a), the template may be the same as or different from a template of a previous repetition, and the template dependent DNA polymerase may be the same as or different from a template dependent DNA polymerase of a previous repetition.

22. The method of claim 21 wherein a template of a repetition of step (a) has a 5' region containing from 1 to about 3 nucleotides and a primer of step (a) of the same repetition is extended by an equal number of complementary nucleotides.

23. The method of claim 21 wherein a template of a repetition of step (a) has a 5' region containing 3 nucleotides and a primer of step (a) of the same repetition is extended by 3 complementary nucleotides.

24. The method of claim 23 wherein said 3 complementary nucleotides represent a codon.

25. A kit comprising multiple populations of templates for directing the synthesis of a polynucleotide comprising repeatedly performing a cycle of steps including;
 (a) annealing a primer having 5' and 3' ends with a template having a 5' region non-complementary to the primer, a 3' region complementary to the 3' end of the primer, the template being shorter than the primer;
 (b) reacting the primer with at least one nucleotide in the presence of a template-dependent polynucleotide polymerase to produce an extended primer including at its 3' end at least one nucleotide complementary to the 5' region of the template; and
 (c) dissociating the template from the extended primer; wherein for each repetition of the cycle the extended primer of step (c) is used as the primer for a next repetition of step (a), the template may be the same as or different from a template of a previous repetition, and the template dependent polynucleotide polymerase may be the same as or different from a template dependent polynucleotide polymerase of a previous repetition, and wherein each of said multiple template populations is disposed in a separate container, and a number of said template populations ranges from 4 to $4^N$.

26. The method of claim 19 wherein a template of a repetition of step (a) has a 5' region containing from 1 to about 10 nucleotides and a primer of step (a) of the same repetition is extended by an equal number of complementary nucleotides.

27. Tile method of claim 19 wherein a template of a repetition of step (a) has a 5' region containing from 1 to about 6 nucleotides and a primer of step (a) of the same repetition is extended by an equal number of complementary nucleotides.

28. The method of claim 19 wherein a template of a repetition of step (a) has a 5' region containing from 1 to about 3 nucleotides and a primer of step (a) of the same repetition is extended by an equal number of complementary nucleotides.

29. The method of claim 19 wherein a template of a repetition of step (a) has a 5' region containing 3 nucleotides and a primer of step (a) of the same repetition is extended by 3 complementary nucleotides.

30. The method of claim 29 wherein said 3 complementary nucleotides represent a codon.

31. The method of claim 19 wherein a template of a repetition of step (a) has a 5' region containing 1 nucleotide and a primer of step (a) of the same repetition is extended by 1 complementary nucleotide.

32. The method of claim 19 wherein a template of a repetition of step (a) is from about 10 to about 20 nucleotides in length.

33. The method of claim 19 wherein a template of a repetition of step (a) has a 3' region containing from 3 to about 19 nucleotides.

34. The method of claim 19 wherein a template of a repetition of step (a) and a template of a next repetition of step (a) each has a 5' region containing the same number of nucleotides.

35. The method of claim 19 wherein a primer of a repetition of step (a) contains from about 12 to about 10,000 nucleotides.

36. The method of claim 19 wherein a primer of a repetition of step (a) comprises a vector polynucleotide.

37. The method of claim 19 wherein a primer of a repetition of step (a) is partially double-stranded.

38. The method of claim 19 wherein a primer of a repetition of step (a) is attached to a solid support.

39. The method of claim 19 wherein said synthesized polynucleotide is a DNA molecule.

40. Tie method of claim 19 wherein said synthesized polynucleotide is a DNA molecule complementary to a nucleic acid molecule or a portion thereof, of interest.

41. The method of claim 19 wherein said synthesized polynucleotide is a gene or a gene segment.

* * * * *

UNITED STATES PATENT AND TRADEMARK OFFICE
CERTIFICATE OF CORRECTION

PATENT NO. : 6,136,568
DATED : October 24, 2000
INVENTOR(S) : Hiatt, et al.

It is certified that error appears in the above-identified patent and that said Letters Patent is hereby corrected as shown below:

Column 10, line 25, "C5S12" should read -- $C5S1^2$ --.

Column 12, line 46, "(TTT..." should read -- (TTT...) ---.

Column 15, line 31, after "1$^{st}$ extension", insert -- 5' ---.

Column 15, line 46, after end of sentence ending with "...ATCGA", insert -- (SEQ ID NO:190) ---.

Column 18, line 7, $sub_1$ should read -- SUB1 --.

Column 20, line 10, "TGANNN9" should read -- TGANN --.

Column 24, line 56, "SEQ ID NO:64" should read -- SEQ ID NO:64) --.

Column 25, line 14, after "GCT3'" insert -- SEQ ID NO:65 --.

UNITED STATES PATENT AND TRADEMARK OFFICE
CERTIFICATE OF CORRECTION

PATENT NO. : 6,136,568
DATED : October 24, 2000
INVENTOR(S) : Hiatt, et al.

It is certified that error appears in the above-identified patent and that said Letters Patent is hereby corrected as shown below:

Column 29, line 14, after "GCT3'" insert - - SEQ ID NO. '88 The corresponding amino acid sequence is designed as SEQ ID NO. '89 - -.

Column 105, line 24, "t he" should read - - the - -.

Column 105, lines 62-63, after "extended" delete - - is extended - -.

Column 105, line 63, "necleotide" should read - - nucleotides - -.

Column 107, line 30, "the" should read - - a - - -.

Signed and Sealed this

First Day of May, 2001

Attest:

NICHOLAS P. GODICI

Attesting Officer          Acting Director of the United States Patent and Trademark Office

UNITED STATES PATENT AND TRADEMARK OFFICE
CERTIFICATE OF CORRECTION

PATENT NO. : 6,136,568
DATED : October 24, 2000
INVENTOR(S) : Hiatt et al.

Page 1 of 1

It is certified that error appears in the above-identified patent and that said Letters Patent is hereby corrected as shown below:

Column 108,
Line 58, "Tie" should read -- The --.

Signed and Sealed this

Twenty-eighth Day of January, 2003

JAMES E. ROGAN
*Director of the United States Patent and Trademark Office*

```
                             SEQUENCE LISTING (1) GENERAL INFORMATION:

(iii) NUMBER OF SEQUENCES: 190

(2) INFORMATION FOR SEQ ID NO:1:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

TCGATCGATC GA                                                         12

(2) INFORMATION FOR SEQ ID NO:2:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

ACGATCGATC G                                                          11

(2) INFORMATION FOR SEQ ID NO:3:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

TCATGGACTC GA                                                         12
```

(2) INFORMATION FOR SEQ ID NO:4:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

ATCATGGACT CG                                                  12

(2) INFORMATION FOR SEQ ID NO:5:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

GATCATGGAC TC                                                  12

(2) INFORMATION FOR SEQ ID NO:6:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

CGATCATGGA CT                                                12

(2) INFORMATION FOR SEQ ID NO:7:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

CATCCATGGA CTC                                             13

(2) INFORMATION FOR SEQ ID NO:8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

ACGCATCATG GA                                                12

(2) INFORMATION FOR SEQ ID NO:9:

(i) SEQUENCE CHARACTERISTICS:
        (A) LENGTH: 12 base pairs (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:9:

CTTACGCATC AT                                                           12

(2) INFORMATION FOR SEQ ID NO:10:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:10:

TCACTTACGC AT                                                           12

(2) INFORMATION FOR SEQ ID NO:11:

(i) SEQUENCE CHARACTERISTICS:
            (A) LENGTH: 16 base pairs
            (B) TYPE: nucleic acid
            (C) STRANDEDNESS: double
            (D) TOPOLOGY: linear (ii) MOLECULE TYPE: DNA (xi) SEQUENCE DESCRIPTION: SEQ ID NO:11:

AGCTAGCTAG CTAGCT                                                       16

(2) INFORMATION FOR SEQ ID NO:12:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: DNA (xi) SEQUENCE DESCRIPTION: SEQ ID NO:12:

AGCTAGCTAG CTAGCTA                                                      17

(2) INFORMATION FOR SEQ ID NO:13:

(i) SEQUENCE CHARACTERISTICS:
            (A) LENGTH: 12 base pairs
            (B) TYPE: nucleic acid
            (C) STRANDEDNESS: double
            (D) TOPOLOGY: linear (ii) MOLECULE TYPE: DNA (xi) SEQUENCE DESCRIPTION: SEQ ID NO:13:

TAGCTAGCTA GC                                                           12

(2) INFORMATION FOR SEQ ID NO:14:

(i) SEQUENCE CHARACTERISTICS:
            (A) LENGTH: 48 base pairs
            (B) TYPE: nucleic acid
            (C) STRANDEDNESS: double
            (D) TOPOLOGY: linear (ii) MOLECULE TYPE: DNA (xi) SEQUENCE DESCRIPTION: SEQ ID NO:14:

AGCTAGCTAG CTAGCTAGCT AGCTAGCTAG CTAGCTAGCT AGCTAGCT                         48

(2) INFORMATION FOR SEQ ID NO:15:

(i) SEQUENCE CHARACTERISTICS:
            (A) LENGTH: 12 base pairs
            (B) TYPE: nucleic acid
            (C) STRANDEDNESS: double
            (D) TOPOLOGY: linear (ii) MOLECULE TYPE: DNA (xi) SEQUENCE DESCRIPTION: SEQ ID NO:15:

AGCTAGCTAG CT                                                                12

(2) INFORMATION FOR SEQ ID NO:16:

(i) SEQUENCE CHARACTERISTICS:
            (A) LENGTH: 48 base pairs
            (B) TYPE: nucleic acid
            (C) STRANDEDNESS: double
            (D) TOPOLOGY: linear (ii) MOLECULE TYPE: DNA (xi) SEQUENCE DESCRIPTION: SEQ ID NO:16:

AGCTAGCTAG CTAGCTAGCT AGCTAGCTAG CTAGCTAGCT AGCTAGCT                         48

(2) INFORMATION FOR SEQ ID NO:17:

(i) SEQUENCE CHARACTERISTICS:
            (A) LENGTH: 12 base pairs
            (B) TYPE: nucleic acid
            (C) STRANDEDNESS: double
            (D) TOPOLOGY: linear (ii) MOLECULE TYPE: DNA (xi) SEQUENCE DESCRIPTION: SEQ ID NO:17:

AGCTAGCTAG CT                                                                12

(2) INFORMATION FOR SEQ ID NO:18:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:18:

AGCTAGCTAG CTAGCTAGCT AGCTAGCTAG CTAGCTAGCT AGCTAGCT                         48

(2) INFORMATION FOR SEQ ID NO:19:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:19:

```
GACTGACTGA CT                                                              12

(2) INFORMATION FOR SEQ ID NO:20:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:20:

AGCTAGCTAG CTAGCT                                                          16

(2) INFORMATION FOR SEQ ID NO:21:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:21:

AGCTAGCTAG CTAGCT                                                          16

(2) INFORMATION FOR SEQ ID NO:22:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:22:

ACGTACGTAC GTACGTACGT                                                      20

(2) INFORMATION FOR SEQ ID NO:23:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:23:

ACGTACGTAC GTACGTACGT                                                      20

(2) INFORMATION FOR SEQ ID NO:24:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:24:

TCAGTCAGTC AG                                                              12

(2) INFORMATION FOR SEQ ID NO:25:
```

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1
        (D) OTHER INFORMATION: /product= "biotin"

(xi) SEQUENCE DESCRIPTION: SEQ ID NO:25:

NCATCAGTAC TGCTCGAGGA ATTCC                                                25

(2) INFORMATION FOR SEQ ID NO:26:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

CGGAATTCCT CGAGCAGTAC TGATC                                                25

(2) INFORMATION FOR SEQ ID NO:27:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

AGGAATTCCT                                                                 10

(2) INFORMATION FOR SEQ ID NO:28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1
        (D) OTHER INFORMATION: /product= "biotin"

(xi) SEQUENCE DESCRIPTION: SEQ ID NO:28:

NAGCATAGGA TCGATGCACT CAGTC                                                25

(2) INFORMATION FOR SEQ ID NO:29:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

AGACTGAGTG                                                              10

(2) INFORMATION FOR SEQ ID NO:30:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

GAGACTGAGT                                                              10

(2) INFORMATION FOR SEQ ID NO:31:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

CGAGACTGAG                                                              10

(2) INFORMATION FOR SEQ ID NO:32:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

TCGAGACTGA                                                              10

(2) INFORMATION FOR SEQ ID NO:33:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

AGACTGNNNN NN                                                           12

(2) INFORMATION FOR SEQ ID NO:34:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

TCTCTCGAGA NNNN                                                         14

(2) INFORMATION FOR SEQ ID NO:35:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

AGACTGNNNN                                                      10

(2) INFORMATION FOR SEQ ID NO:36:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

AGACNNNNNN                                                      10

(2) INFORMATION FOR SEQ ID NO:37:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

AGACTGNNNN NN                                               12

(2) INFORMATION FOR SEQ ID NO:38:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

ACTGACNNNN                                                    10

(2) INFORMATION FOR SEQ ID NO:39:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

ACTGACNNNN N                                                11

(2) INFORMATION FOR SEQ ID NO:40:

(i) SEQUENCE CHARACTERISTICS:

(A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

ACTGACNNNN NN                                                                12

(2) INFORMATION FOR SEQ ID NO:41:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

ACTGACTGNN NN                                                                12

(2) INFORMATION FOR SEQ ID NO:42:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:42:

TCAGACTGAN NNNNN                                                             15

(2) INFORMATION FOR SEQ ID NO:43:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:43:

TCAGACTGAN NNNN                                                              14

(2) INFORMATION FOR SEQ ID NO:44:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:44:

TCAGACTGAN NNN                                                               13

(2) INFORMATION FOR SEQ ID NO:45:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:45:

CAACTGAGTG                                                                      10

(2) INFORMATION FOR SEQ ID NO:46:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:46:

CGGCTGAGTG                                                                      10

(2) INFORMATION FOR SEQ ID NO:47:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:47:

CGATTGAGTG                                                                      10

(2) INFORMATION FOR SEQ ID NO:48:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:48:

CGACCGAGTG                                                                      10

(2) INFORMATION FOR SEQ ID NO:49:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:49:

CGACTAAGTG                                                                      10

(2) INFORMATION FOR SEQ ID NO:50:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:

(A) NAME/KEY: misc_feature
            (B) LOCATION: 1
            (D) OTHER INFORMATION: /product= "phosphate"

(ix) FEATURE:
            (A) NAME/KEY: misc_feature
            (B) LOCATION: 13
            (D) OTHER INFORMATION: /product= "biotin"

(xi) SEQUENCE DESCRIPTION: SEQ ID NO:50:

NTATGGATCC TCNATGCACT CAGTC                                              25

(2) INFORMATION FOR SEQ ID NO:51:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:51:

ATAGATCTCG AGGATCCATA                                                    20

(2) INFORMATION FOR SEQ ID NO:52:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1
            (D) OTHER INFORMATION: /product= "biotin"

(xi) SEQUENCE DESCRIPTION: SEQ ID NO:52:

NATGGATCCT CGAGATCTAT GAAG                                               24

(2) INFORMATION FOR SEQ ID NO:53:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:53:

ACAGTTCTTC ATAGA                                                         15

(2) INFORMATION FOR SEQ ID NO:54:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:54:

TTTGCAGTTC TTCAT                                                         15

(2) INFORMATION FOR SEQ ID NO:55:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:55:

CTCGAGGCAG TTCTT         15

(2) INFORMATION FOR SEQ ID NO:56:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:56:

TCTGAGGAGG CAGTT         15

(2) INFORMATION FOR SEQ ID NO:57:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:57:

CTTGAAGAGG AGGCA         15

(2) INFORMATION FOR SEQ ID NO:58:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:58:

TTGCCAGAAG AGGAG         15

(2) INFORMATION FOR SEQ ID NO:59:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:59:

GAGTCCCCAG AAGAG         15

(2) INFORMATION FOR SEQ ID NO:60:

(i) SEQUENCE CHARACTERISTICS:
        (A) LENGTH: 15 base pairs

```
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:60:

TGTCACTCCC CAGAA                                                          15

(2) INFORMATION FOR SEQ ID NO:61:

(i) SEQUENCE CHARACTERISTICS:
              (A) LENGTH: 15 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:61:

CCTGAGCACT CCCCA                                                          15

(2) INFORMATION FOR SEQ ID NO:62:

(i) SEQUENCE CHARACTERISTICS:
              (A) LENGTH: 15 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:62:

TTTAGCGAGC ACTCC                                                          15

(2) INFORMATION FOR SEQ ID NO:63:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:63:

AACTGCCTCC TCTTCTGGGG AGTGCTCGCT                                          30

(2) INFORMATION FOR SEQ ID NO:64:

(i) SEQUENCE CHARACTERISTICS:
              (A) LENGTH: 13 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: misc_feature
              (B) LOCATION: 1
              (D) OTHER INFORMATION: /product= "biotin"

(xi) SEQUENCE DESCRIPTION: SEQ ID NO:64:

NGACATTGTG ATG                                                            13

(2) INFORMATION FOR SEQ ID NO:65:

(i) SEQUENCE CHARACTERISTICS:
```

(A) LENGTH: 342 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..342

(xi) SEQUENCE DESCRIPTION: SEQ ID NO:65:

```
GAC ATT GTG ATG TCA CAG TCT CCA TCC TCC CTG GCT GTG TCA GCA GGA         48
Asp Ile Val Met Ser Gln Ser Pro Ser Ser Leu Ala Val Ser Ala Gly
  1               5                  10                  15

GAG AAG GTC ACT ATG AGC TGC AAA TCC AGT CAG AGT CTG CTC AAC AGT         96
Glu Lys Val Thr Met Ser Cys Lys Ser Ser Gln Ser Leu Leu Asn Ser
             20                  25                  30

ATA ACC CGA AAG AAC TTC TTG GCT TGG TAC CAG CAG AAA CCA GGG CAG        144
Ile Thr Arg Lys Asn Phe Leu Ala Trp Tyr Gln Gln Lys Pro Gly Gln
         35                  40                  45

TCT CCT AAA CTG CTG ATC TAC TGG GCA TCC ACT AGG GAA TCT GGG GTC        192
Ser Pro Lys Leu Leu Ile Tyr Trp Ala Ser Thr Arg Glu Ser Gly Val
     50                  55                  60

CCT GAT CGC TTC ACA GGC AGT GGA TCT GGG ACA GAT TTC ACT CTC ACC        240
Pro Asp Arg Phe Thr Gly Ser Gly Ser Gly Thr Asp Phe Thr Leu Thr
 65                  70                  75                  80

ATC AGC AGT GTG CAG GCT GAA GAC CTG GCA GTT TAT TAC TGC AAG CAA        288
Ile Ser Ser Val Gln Ala Glu Asp Leu Ala Val Tyr Tyr Cys Lys Gln
                 85                  90                  95

TCT TAT AAT CTT CGG ACG TTC GGT GGA GGC ACC AAG CTG GAA ATC AAA        336
Ser Tyr Asn Leu Arg Thr Phe Gly Gly Gly Thr Lys Leu Glu Ile Lys
                100                 105                 110

CGG GCT                                                                342
Arg Ala
```

(2) INFORMATION FOR SEQ ID NO:66:

(i) SEQUENCE CHARACTERISTICS:
        (A) LENGTH: 114 amino acids
        (B) TYPE: amino acid
        (D) TOPOLOGY: linear (ii) MOLECULE TYPE: protein (xi) SEQUENCE DESCRIPTION: SEQ ID NO:66:

```
Asp Ile Val Met Ser Gln Ser Pro Ser Ser Leu Ala Val Ser Ala Gly
  1               5                  10                  15

Glu Lys Val Thr Met Ser Cys Lys Ser Ser Gln Ser Leu Leu Asn Ser
             20                  25                  30

Ile Thr Arg Lys Asn Phe Leu Ala Trp Tyr Gln Gln Lys Pro Gly Gln
         35                  40                  45

Ser Pro Lys Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Tyr Asn Leu Arg Thr Phe Gly Gly Gly Thr Lys Leu Glu Ile Lys
                100                 105                 110

Arg Ala
```

(2) INFORMATION FOR SEQ ID NO:67:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:67:

TGACATCACN NN                                                  12

(2) INFORMATION FOR SEQ ID NO:68:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:68:

CTGTGACATN NN                                                  12

(2) INFORMATION FOR SEQ ID NO:69:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:69:

AGACTGTGAN NN                                                  12

(2) INFORMATION FOR SEQ ID NO:70:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:70:

TGGAGACTGN NN                                                  12

(2) INFORMATION FOR SEQ ID NO:71:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:71:

GGATGGAGAN NN                                                  12

(2) INFORMATION FOR SEQ ID NO:72:

(i) SEQUENCE CHARACTERISTICS:

(A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:72:

GGAGGATGGN NN                                                               12

(2) INFORMATION FOR SEQ ID NO:73:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:73:

CAGGGAGGAN NN                                                               12

(2) INFORMATION FOR SEQ ID NO:74:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:74:

AGCCAGGGAN NN                                                               12

(2) INFORMATION FOR SEQ ID NO:75:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:75:

CACAGCCAGN NN                                                               12

(2) INFORMATION FOR SEQ ID NO:76:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:76:

TGACACAGCN NN                                                               12

(2) INFORMATION FOR SEQ ID NO:77:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:77:

TGCTGACACN NN                                                                  12

(2) INFORMATION FOR SEQ ID NO:78:

(i) SEQUENCE CHARACTERISTICS:
              (A) LENGTH: 12 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:78:

TCCTGCTGAN NN                                                                  12

(2) INFORMATION FOR SEQ ID NO:79:

(i) SEQUENCE CHARACTERISTICS:
              (A) LENGTH: 12 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:79:

CTCTCCTGCN NN                                                                  12

(2) INFORMATION FOR SEQ ID NO:80:

(i) SEQUENCE CHARACTERISTICS:
              (A) LENGTH: 12 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:80:

CTTCTCTCCN NN                                                                  12

(2) INFORMATION FOR SEQ ID NO:81:

(i) SEQUENCE CHARACTERISTICS:
              (A) LENGTH: 12 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:81:

GACCTTCTCN NN                                                                  12

(2) INFORMATION FOR SEQ ID NO:82:

(i) SEQUENCE CHARACTERISTICS:
              (A) LENGTH: 12 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:82:

```
AGTGACCTTN NN                                                           12
```

(2) INFORMATION FOR SEQ ID NO:83:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:83:

```
CATAGTGACN NN                                                           12
```

(2) INFORMATION FOR SEQ ID NO:84:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:84:

```
GCTCATAGTN NN                                                           12
```

(2) INFORMATION FOR SEQ ID NO:85:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:85:

```
GCAGCTCATN NN                                                           12
```

(2) INFORMATION FOR SEQ ID NO:86:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:86:

```
TTTGCAGCTN NN                                                           12
```

(2) INFORMATION FOR SEQ ID NO:87:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:87:

```
GGATTTGCAN NN                                                           12
```

(2) INFORMATION FOR SEQ ID NO:88:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:88:

ACTGGATTTN NN                                                             12

(2) INFORMATION FOR SEQ ID NO:89:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:89:

CTGACTGGAN NN                                                             12

(2) INFORMATION FOR SEQ ID NO:90:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:90:

ACTCTGACTN NN                                                             12

(2) INFORMATION FOR SEQ ID NO:91:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:91:

CAGACTCTGN NN                                                             12

(2) INFORMATION FOR SEQ ID NO:92:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:92:

GAGCAGACTN NN                                                            12

(2) INFORMATION FOR SEQ ID NO:93:

(i) SEQUENCE CHARACTERISTICS:
        (A) LENGTH: 12 base pairs (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:93:

GTTGAGCAGN NN                                                            12

(2) INFORMATION FOR SEQ ID NO:94:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:94:

ACTGTTGAGN NN                                                            12

(2) INFORMATION FOR SEQ ID NO:95:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:95:

TATACTGTTN NN                                                            12

(2) INFORMATION FOR SEQ ID NO:96:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:96:

GGTTATACTN NN                                                            12

(2) INFORMATION FOR SEQ ID NO:97:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:97:

TCGGGTTATN NN                                                            12

(2) INFORMATION FOR SEQ ID NO:98:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:98:

CTTTCGGGTN NN                                                                         12

(2) INFORMATION FOR SEQ ID NO:99:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:99:

GTTCTTTCGN NN                                                                         12

(2) INFORMATION FOR SEQ ID NO:100:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:100:

GAAGTTCTTN NN                                                                         12

(2) INFORMATION FOR SEQ ID NO:101:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:101:

CAAGAAGTTN NN                                                                         12

(2) INFORMATION FOR SEQ ID NO:102:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:102:

AGCCAAGAAN NN                                                                         12

(2) INFORMATION FOR SEQ ID NO:103:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:103:

```
CCAAGCCAAN NN                                                               12

(2) INFORMATION FOR SEQ ID NO:104:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:104:

GTACCAAGCN NN                                                               12

(2) INFORMATION FOR SEQ ID NO:105:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:105:

CTGGTACCAN NN                                                               12

(2) INFORMATION FOR SEQ ID NO:106:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:106:

CTGCTGGTAN NN                                                               12

(2) INFORMATION FOR SEQ ID NO:107:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:107:

TTTCTGCTGN NN                                                               12

(2) INFORMATION FOR SEQ ID NO:108:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:108:

TGGTTTCTGN NN                                                               12

(2) INFORMATION FOR SEQ ID NO:109:
```

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:109:

CCCTGGTTTN NN                                                            12

(2) INFORMATION FOR SEQ ID NO:110:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:110:

CTGCCCTGGN NN                                                            12

(2) INFORMATION FOR SEQ ID NO:111:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:111:

AGACTGCCCN NN                                                            12

(2) INFORMATION FOR SEQ ID NO:112:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:112:

AGGAGACTGN NN                                                            12

(2) INFORMATION FOR SEQ ID NO:113:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:113:

TTTAGGAGAN NN                                                            12

(2) INFORMATION FOR SEQ ID NO:114:

(i) SEQUENCE CHARACTERISTICS:
    (A) LENGTH: 12 base pairs
    (B) TYPE: nucleic acid

```
            (C) STRANDEDNESS: single
            (D) TOPOLOGY: linear (ii) MOLECULE TYPE: DNA (xi) SEQUENCE DESCRIPTION: SEQ ID NO:114:

CAGTTTAGGN NN                                                              12

(2) INFORMATION FOR SEQ ID NO:115:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:115:

CAGCAGTTTN NN                                                              12

(2) INFORMATION FOR SEQ ID NO:116:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:116:

GATCAGCAGN NN                                                              12

(2) INFORMATION FOR SEQ ID NO:117:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:117:

GTAGATCAGN NN                                                              12

(2) INFORMATION FOR SEQ ID NO:118:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:118:

CCAGTAGATN NN                                                              12

(2) INFORMATION FOR SEQ ID NO:119:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA
```

(xi) SEQUENCE DESCRIPTION: SEQ ID NO:119:

TGCCCAGTAN NN                                                         12

(2) INFORMATION FOR SEQ ID NO:120:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:120:

GGATGCCCAN NN                                                         12

(2) INFORMATION FOR SEQ ID NO:121:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:121:

AGTGGATGCN NN                                                         12

(2) INFORMATION FOR SEQ ID NO:122:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:122:

CCTAGTGGAN NN                                                         12

(2) INFORMATION FOR SEQ ID NO:123:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:123:

TTCCCTAGTN NN                                                         12

(2) INFORMATION FOR SEQ ID NO:124:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:124:

AGATTCCCTN NN                                                         12

(2) INFORMATION FOR SEQ ID NO:125:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:125:

CCCAGATTCN NN                                                        12

(2) INFORMATION FOR SEQ ID NO:126:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:126:

GACCCCAGAN NN                                                        12

(2) INFORMATION FOR SEQ ID NO:127:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:127:

AGGGACCCCN NN                                                        12

(2) INFORMATION FOR SEQ ID NO:128:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:128:

ATCAGGGACN NN                                                        12

(2) INFORMATION FOR SEQ ID NO:129:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:129:

GCGATCAGGN NN                                                        12

(2) INFORMATION FOR SEQ ID NO:130:

```
    (i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:130:

GAAGCGATCN NN                                                              12

(2) INFORMATION FOR SEQ ID NO:131:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:131:

TGTGAAGCGN NN                                                              12

(2) INFORMATION FOR SEQ ID NO:132:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:132:

GCCTGTGAAN NN                                                              12

(2) INFORMATION FOR SEQ ID NO:133:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:133:

ACTGCCTGTN NN                                                              12

(2) INFORMATION FOR SEQ ID NO:134:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:134:

TCCACTGCCN NN                                                              12

(2) INFORMATION FOR SEQ ID NO:135:

(i) SEQUENCE CHARACTERISTICS:
        (A) LENGTH: 12 base pairs
        (B) TYPE: nucleic acid
        (C) STRANDEDNESS: single
```

(D) TOPOLOGY: linear (ii) MOLECULE TYPE: DNA (xi) SEQUENCE DESCRIPTION: SEQ ID NO:135:

AGATCCACTN NN                                                              12

(2) INFORMATION FOR SEQ ID NO:136:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:136:

CCCAGATCCN NN                                                              12

(2) INFORMATION FOR SEQ ID NO:137:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:137:

TGTCCCAGAN NN                                                              12

(2) INFORMATION FOR SEQ ID NO:138:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:138:

ATCTGTCCCN NN                                                              12

(2) INFORMATION FOR SEQ ID NO:139:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:139:

GAAATCTGTN NN                                                              12

(2) INFORMATION FOR SEQ ID NO:140:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA

```
    (xi) SEQUENCE DESCRIPTION: SEQ ID NO:140:

AGTGAAATCN NN                                                              12

(2) INFORMATION FOR SEQ ID NO:141:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:141:

GAGAGTGAAN NN                                                              12

(2) INFORMATION FOR SEQ ID NO:142:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:142:

GGTGAGAGTN NN                                                              12

(2) INFORMATION FOR SEQ ID NO:143:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:143:

GATGGTGAGN NN                                                              12

(2) INFORMATION FOR SEQ ID NO:144:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:144:

GCTGATGGTN NN                                                              12

(2) INFORMATION FOR SEQ ID NO:145:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:145:

ACTGCTGATN NN                                                              12
```

(2) INFORMATION FOR SEQ ID NO:146:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:146:

CACACTGCTN NN                                                            12

(2) INFORMATION FOR SEQ ID NO:147:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:147:

CTGCACACTN NN                                                            12

(2) INFORMATION FOR SEQ ID NO:148:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:148:

AGCCTGCACN NN                                                            12

(2) INFORMATION FOR SEQ ID NO:149:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:149:

TTCAGCCTGN NN                                                           12

(2) INFORMATION FOR SEQ ID NO:150:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:150:

GTCTTCAGCN NN                                                           12

(2) INFORMATION FOR SEQ ID NO:151:

(i) SEQUENCE CHARACTERISTICS:

(A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:151:

CAGGTCTTCN NN                                                               12

(2) INFORMATION FOR SEQ ID NO:152:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:152:

TGCCAGGTCN NN                                                               12

(2) INFORMATION FOR SEQ ID NO:153:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:153:

AACTGCCAGN NN                                                               12

(2) INFORMATION FOR SEQ ID NO:154:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:154:

ATAAACTGCN NN                                                               12

(2) INFORMATION FOR SEQ ID NO:155:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:155:

GTAATAAACN NN                                                               12

(2) INFORMATION FOR SEQ ID NO:156:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:156:

GCAGTAATAN NN                                                                    12

(2) INFORMATION FOR SEQ ID NO:157:

(i) SEQUENCE CHARACTERISTICS:
              (A) LENGTH: 12 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:157:

CTTGCAGTAN NN                                                                    12

(2) INFORMATION FOR SEQ ID NO:158:

(i) SEQUENCE CHARACTERISTICS:
              (A) LENGTH: 12 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:158:

TTGCTTGCAN NN                                                                    12

(2) INFORMATION FOR SEQ ID NO:159:

(i) SEQUENCE CHARACTERISTICS:
              (A) LENGTH: 12 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:159:

AGATTGCTTN NN                                                                    12

(2) INFORMATION FOR SEQ ID NO:160:

(i) SEQUENCE CHARACTERISTICS:
              (A) LENGTH: 12 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:160:

ATAAGATTGN NN                                                                    12

(2) INFORMATION FOR SEQ ID NO:161:

(i) SEQUENCE CHARACTERISTICS:
              (A) LENGTH: 12 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:161:

ATTATAAGAN NN                                                        12

(2) INFORMATION FOR SEQ ID NO:162:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:162:

AAGATTATAN NN                                                        12

(2) INFORMATION FOR SEQ ID NO:163:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:163:

CCGAAGATTN NN                                                        12

(2) INFORMATION FOR SEQ ID NO:164:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:164:

CGTCCGAAGN NN                                                        12

(2) INFORMATION FOR SEQ ID NO:165:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:165:

GAACGTCCGN NN                                                        12

(2) INFORMATION FOR SEQ ID NO:166:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:166:

ACCGAACGTN NN                                                        12

```
(2) INFORMATION FOR SEQ ID NO:167:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:167:

TCCACCGAAN NN                                                                12

(2) INFORMATION FOR SEQ ID NO:168:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:168:

GCCTCCACCN NN                                                                12

(2) INFORMATION FOR SEQ ID NO:169:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:169:

GGTGCCTCCN NN                                                                12

(2) INFORMATION FOR SEQ ID NO:170:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:170:

CTTGGTGCCN NN                                                                12

(2) INFORMATION FOR SEQ ID NO:171:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:171:

CAGCTTGGTN NN                                                                12

(2) INFORMATION FOR SEQ ID NO:172:

(i) SEQUENCE CHARACTERISTICS:
         (A) LENGTH: 12 base pairs
```

```
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:172:

TTCCAGCTTN NN                                                           12

(2) INFORMATION FOR SEQ ID NO:173:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:173:

GATTTCCAGN NN                                                           12

(2) INFORMATION FOR SEQ ID NO:174:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:174:

TTTGATTTCN NN                                                           12

(2) INFORMATION FOR SEQ ID NO:175:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:175:

CCGTTTGATN NN                                                           12

(2) INFORMATION FOR SEQ ID NO:176:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:176:

AGCCCGTTTN NN                                                           12

(2) INFORMATION FOR SEQ ID NO:177:

(i) SEQUENCE CHARACTERISTICS:
            (A) LENGTH: 12 base pairs
            (B) TYPE: nucleic acid
            (C) STRANDEDNESS: single
            (D) TOPOLOGY: linear
```

(ii) MOLECULE TYPE: DNA (xi) SEQUENCE DESCRIPTION: SEQ ID NO:177:

TTCACTGGAN NN                                                                                  12

(2) INFORMATION FOR SEQ ID NO:178:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:178:

GCCTTGACTN NN                                                                                  12

(2) INFORMATION FOR SEQ ID NO:179:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:179:

CAGGCCTTCN NN                                                                                  12

(2) INFORMATION FOR SEQ ID NO:180:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:180:

GAGCAGGCCN NN                                                                                  12

(2) INFORMATION FOR SEQ ID NO:181:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:181:

AAAGTAGATN NN                                                                                  12

(2) INFORMATION FOR SEQ ID NO:182:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:182:

TGCAAAGTAN NN                                                        12

(2) INFORMATION FOR SEQ ID NO:183:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:183:

GGATGCAAAN NN                                                        12

(2) INFORMATION FOR SEQ ID NO:184:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:184:

ATGGCAGTAN NN                                                        12

(2) INFORMATION FOR SEQ ID NO:185:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:185:

ATTATGGCAN NN                                                        12

(2) INFORMATION FOR SEQ ID NO:186:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:186:

AGAATTATGN NN                                                        12

(2) INFORMATION FOR SEQ ID NO:187:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:187:

ATAAGAATTN NN                                                        12

(2) INFORMATION FOR SEQ ID NO:188:

(i) SEQUENCE CHARACTERISTICS:
    (A) LENGTH: 342 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 1..342

(xi) SEQUENCE DESCRIPTION: SEQ ID NO:188:

| GAC | ATT | GTG | ATG | TCA | CAG | TCT | CCA | TCC | TCC | CTG | GCT | GTG | TCA | GCA | GGA | 48 |
|---|---|---|---|---|---|---|---|---|---|---|---|---|---|---|---|---|
| Asp | Ile | Val | Met | Ser | Gln | Ser | Pro | Ser | Ser | Leu | Ala | Val | Ser | Ala | Gly | |
| 1 | | | | 5 | | | | | 10 | | | | | 15 | | |

| GAG | AAG | GTC | ACT | ATG | AGC | TGC | AAA | TCC | AGT | GAA | GGC | CTG | CTC | AAC | AGT | 96 |
|---|---|---|---|---|---|---|---|---|---|---|---|---|---|---|---|---|
| Glu | Lys | Val | Thr | Met | Ser | Cys | Lys | Ser | Ser | Glu | Gly | Leu | Leu | Asn | Ser | |
| | | | 20 | | | | | 25 | | | | | 30 | | | |

| ATA | ACC | CGA | AAG | AAC | TTC | TTG | GCT | TGG | TAC | CAG | CAG | AAA | CCA | GGG | CAG | 144 |
|---|---|---|---|---|---|---|---|---|---|---|---|---|---|---|---|---|
| Ile | Thr | Arg | Lys | Asn | Phe | Leu | Ala | Trp | Tyr | Gln | Gln | Lys | Pro | Gly | Gln | |
| | | 35 | | | | | 40 | | | | | 45 | | | | |

| TCT | CCT | AAA | CTG | CTG | ATC | TAC | TTT | GCA | TCC | ACT | AGG | GAA | TCT | GGG | GTC | 192 |
|---|---|---|---|---|---|---|---|---|---|---|---|---|---|---|---|---|
| Ser | Pro | Lys | Leu | Leu | Ile | Tyr | Phe | Ala | Ser | Thr | Arg | Glu | Ser | Gly | Val | |
| 50 | | | | | 55 | | | | | 60 | | | | | | |

| CCT | GAT | CGC | TTC | ACA | GGC | AGT | GGA | TCT | GGG | ACA | GAT | TTC | ACT | CTC | ACC | 240 |
|---|---|---|---|---|---|---|---|---|---|---|---|---|---|---|---|---|
| Pro | Asp | Arg | Phe | Thr | Gly | Ser | Gly | Ser | Gly | Thr | Asp | Phe | Thr | Leu | Thr | |
| 65 | | | | | 70 | | | | | 75 | | | | | 80 | |

| ATC | AGC | AGT | GTG | CAG | GCT | GAA | GAC | CTG | GCA | GTT | TAT | TAC | TGC | CAT | AAT | 288 |
|---|---|---|---|---|---|---|---|---|---|---|---|---|---|---|---|---|
| Ile | Ser | Ser | Val | Gln | Ala | Glu | Asp | Leu | Ala | Val | Tyr | Tyr | Cys | His | Asn | |
| | | | | 85 | | | | | 90 | | | | | 95 | | |

| TCT | TAT | AAT | CTT | CGG | ACG | TTC | GGT | GGA | GGC | ACC | AAG | CTG | GAA | ATC | AAA | 336 |
|---|---|---|---|---|---|---|---|---|---|---|---|---|---|---|---|---|
| Ser | Tyr | Asn | Leu | Arg | Thr | Phe | Gly | Gly | Gly | Thr | Lys | Leu | Glu | Ile | Lys | |
| | | | 100 | | | | | 105 | | | | | 110 | | | |

| CGG | GCT | | | | | | | | | | | | | | | 342 |
|---|---|---|---|---|---|---|---|---|---|---|---|---|---|---|---|---|
| Arg | Ala | | | | | | | | | | | | | | | |

(2) INFORMATION FOR SEQ ID NO:189:

(i) SEQUENCE CHARACTERISTICS:
        (A) LENGTH: 114 amino acids
        (B) TYPE: amino acid
        (D) TOPOLOGY: linear (ii) MOLECULE TYPE: protein (xi) SEQUENCE DESCRIPTION: SEQ ID NO:189:

Asp Ile Val Met Ser Gln Ser Pro Ser Ser Leu Ala Val Ser Ala Gly
 1               5                  10                  15

Glu Lys Val Thr Met Ser Cys Lys Ser Ser Glu Gly Leu Leu Asn Ser
                20                  25                  30

Ile Thr Arg Lys Asn Phe Leu Ala Trp Tyr Gln Gln Lys Pro Gly Gln
            35                  40                  45

Ser Pro Lys Leu Leu Ile Tyr Phe Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys His Asn
                85                  90                  95

Ser Tyr Asn Leu Arg Thr Phe Gly Gly Gly Thr Lys Leu Glu Ile Lys
            100                 105                 110

```
-continued
Arg Ala (2) INFORMATION FOR SEQ ID NO:190:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:190:

AGCTAGCTAG CTAGCTAGCT AGCTAGCTAG CTAGCT                                36
```